(12) United States Patent
Yamada et al.

(10) Patent No.: US 10,869,503 B2
(45) Date of Patent: Dec. 22, 2020

(54) NON-BURNING-TYPE FLAVOR INHALER AND COMPUTER-READABLE MEDIUM

(71) Applicant: JAPAN TOBACCO INC., Tokyo (JP)

(72) Inventors: Manabu Yamada, Tokyo (JP);
Manabu Takeuchi, Tokyo (JP);
Hirofumi Matsumoto, Tokyo (JP);
Masafumi Tarora, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 654 days.

(21) Appl. No.: 15/340,152

(22) Filed: Nov. 1, 2016

(65) Prior Publication Data

US 2017/0042251 A1    Feb. 16, 2017

Related U.S. Application Data

(63) Continuation of application No. PCT/JP2015/062850, filed on Apr. 28, 2015.

(30) Foreign Application Priority Data

May 2, 2014    (JP) ................................ 2014-095160

(51) Int. Cl.
*A24F 47/00* (2020.01)
*H05B 1/02* (2006.01)
(Continued)

(52) U.S. Cl.
CPC ............ *A24F 47/008* (2013.01); *A24F 47/00* (2013.01); *A61M 11/042* (2014.02);
(Continued)

(58) Field of Classification Search
CPC .......... A24F 15/12; A24F 15/14; A24F 15/18; A24F 47/00; A24F 47/002; A24F 47/008;
(Continued)

(56) References Cited

U.S. PATENT DOCUMENTS 5,060,671 A     10/1991 Counts et al.
2009/0320863 A1    12/2009 Fernando et al.
(Continued)

FOREIGN PATENT DOCUMENTS

CN    103415222 A    11/2013
EA    201390961 A    1/2014
(Continued)

OTHER PUBLICATIONS

Japanese Office Action, dated Jul. 31, 2018, for corresponding Japanese Application No. 2017-124463, with an English machine translation.
(Continued)

*Primary Examiner* — Justin C Dodson
(74) *Attorney, Agent, or Firm* — Birch, Stewart, Kolasch & Birch, LLP

(57) ABSTRACT

A non-burning type flavor inhaler comprises: a first unit; a second unit including an aerosol source or a flavor source; and a control unit. The control unit integrates a first cumulative amount of electric power which is a cumulative value of the amount of electric power supplied to the heat source in the one-time puff action series, and the control unit notifies an end of the one-time puff action series when the first cumulative amount of electric power reaches the required amount of electric power.

12 Claims, 15 Drawing Sheets

(51) Int. Cl.
*A61M 11/04* (2006.01)
*A61M 15/06* (2006.01)
*A61M 15/00* (2006.01)
A61M 16/00 (2006.01)

(52) U.S. Cl.
CPC .......... *A61M 15/003* (2014.02); *A61M 15/06* (2013.01); *H05B 1/0244* (2013.01); *A61M 15/0021* (2014.02); *A61M 15/0036* (2014.02); *A61M 2016/0024* (2013.01); *A61M 2205/3317* (2013.01); *A61M 2205/587* (2013.01); *A61M 2205/8206* (2013.01); *H05B 2203/021* (2013.01)

(58) Field of Classification Search
CPC .......... H05B 3/0014; H05B 3/10; H05B 3/16; H05B 3/42; H05B 1/0244; H05B 2203/003; A61M 15/06; A61M 15/0021; A61M 2016/0024; A61M 2205/3317; A61M 2205/587; A61M 2205/8206; A61M 11/042
USPC ....... 392/386, 394, 403, 405, 406, 395, 404; 131/185, 193, 194, 329, 330
See application file for complete search history.

(56) References Cited

U.S. PATENT DOCUMENTS

| | | |
|---|---|---|
| 2011/0265806 A1 | 11/2011 | Alarcon et al. |
| 2012/0048266 A1 | 3/2012 | Alelov |
| 2013/0319440 A1 | 12/2013 | Capuano |
| 2014/0020693 A1* | 1/2014 | Cochand .............. A61M 11/041 131/273 |
| 2014/0096782 A1* | 4/2014 | Ampolini .............. A24F 47/008 131/328 |
| 2014/0299141 A1 | 10/2014 | Flick |
| 2015/0047656 A1 | 2/2015 | Robinson et al. |
| 2016/0206005 A1 | 7/2016 | Yamada et al. |

FOREIGN PATENT DOCUMENTS

| | | |
|---|---|---|
| EP | 0 845 220 A1 | 6/1998 |
| JP | 7-184627 A | 7/1995 |
| JP | 2010-506594 A | 3/2010 |
| JP | 2011-517567 A | 6/2011 |
| JP | 2014-501106 A | 1/2014 |
| TW | 201322936 A1 | 6/2013 |
| WO | WO 94/06314 A1 | 3/1994 |
| WO | WO 97/48293 A1 | 12/1997 |
| WO | WO 98/17131 A1 | 4/1998 |
| WO | WO 2012/085205 A1 | 6/2012 |
| WO | WO 2012/162305 A1 | 11/2012 |
| WO | WO 2013/102611 A2 | 7/2013 |
| WO | WO 2015/046420 A1 | 4/2015 |

OTHER PUBLICATIONS

Eurasian Office Action, dated Jun. 27, 2018, for Eurasian Application No. 201692211, along with an English translation.
International Search Report for PCT/JP2015/062850 (PCT/ISA/210) dated Aug. 18, 2015.
Eurasian Office Action dated Dec. 10, 2018 for Application No. 201692211/31, along with an English translation.
Extended European Search Report for European Application No. 15786326.7, dated Dec. 13, 2017.
Japanese Decision of Dismissal, dated Apr. 3, 2020, for Japanese Application No. 2017-124463, with an English transtation.
Japanese Office Action, dated Mar. 25, 2020, for Japanese Application No. 2017-124463, with an English translation.

* cited by examiner

FIG. 4

| PUFFING STATE | NON-PUFFING STATE #1 | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|---|
| LIGHT-EMITTING MODE | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 | LIGHT-EMITTING MODE #2-1 | LIGHT-EMITTING MODE #1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-2 | LIGHT-EMITTING MODE #1 | LIGHT-EMITTING MODE #2-3 | LIGHT-EMITTING MODE #1 | END LIGHT-EMITTING MODE | LIGHT-EMITTING MODE #1 |

FIG. 5

| PUFFING STATE | PUFFING STATE #1 | NON-PUFFING STATE #2 | PUFFING STATE #2 | NON-PUFFING STATE #3 | PUFFING STATE #3 | NON-PUFFING STATE #4 | PUFFING STATE #4 |
|---|---|---|---|---|---|---|---|
| LIGHT-EMITTING MODE | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #2-1 | LIGHT-EMITTING MODE #1-1 | LIGHT-EMITTING MODE #1-1 |

| PUFFING STATE | NON-PUFFING STATE #5 | PUFFING STATE #5 | NON-PUFFING STATE #6 | PUFFING STATE #6 | NON-PUFFING STATE #7 | PUFFING STATE #7 | NON-PUFFING STATE #8 | PUFFING STATE #8 | NON-PUFFING STATE #9 AND THEREAFTER | PUFFING STATE #9 AND THEREAFTER |
|---|---|---|---|---|---|---|---|---|---|---|
| LIGHT-EMITTING MODE | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-2 | LIGHT-EMITTING MODE #1-2 | LIGHT-EMITTING MODE #2-3 | LIGHT-EMITTING MODE #1-3 | END LIGHT-EMITTING MODE | LIGHT-EMITTING MODE #1-4 |

NON-BURNING-TYPE FLAVOR INHALER AND COMPUTER-READABLE MEDIUM

CROSS REFERENCE TO RELATED APPLICATIONS

This application is a Continuation of PCT International Application No. PCT/JP2015/062850, filed on Apr. 28, 2015, which claims priority under 35 U.S.C. 119(a) to Patent Application No. 2014-095160, filed in Japan on May 2, 2014, all of which are hereby expressly incorporated by reference into the present application.

TECHNICAL FIELD

The present invention relates to a non-burning type flavor inhaler having a shape extending along a predetermined direction from a non-mouthpiece end toward a mouthpiece end, and a computer-readable medium.

BACKGROUND ART

Conventionally, there is known a non-burning type flavor inhaler for inhaling flavor without burning. The non-burning type flavor inhaler has a shape extending along a predetermined direction from a non-mouthpiece end toward a mouthpiece end. The non-burning type flavor inhaler has an aerosol source configured to generate aerosol, a heat source configured to heat the aerosol source without burning, and a power source configured to supply electric power to the heat source (Patent Document 1).

PRIOR ART DOCUMENT

Patent Document

Patent Document 1: JP 2010-506594 A

SUMMARY

A first feature is summarized as a non-burning type flavor inhaler having a shape extending along a predetermined direction from a non-mouthpiece end toward a mouthpiece end, comprising: a first unit having the non-mouthpiece end; a second unit attached to the first unit; and a control unit configured to control the non-burning type flavor inhaler, wherein the second unit includes an aerosol source generating aerosol or a flavor source, the non-burning type flavor inhaler includes a heat source configured to heat the aerosol source or the flavor source without burning, and a power source configured to supply electric power to the heat source, a permissible amount of electric power defined by a cumulative value of an amount of electric power that is permitted to be supplied to the heat source after attaching the second unit to the first unit is larger than a required amount of electric power defined by a cumulative value of an amount of electric power to be supplied to the heat source in a one-time puff action series which is a series of actions in which a puff action is repeated a predetermined number of times, the permissible amount of electric power is a condition for appropriately using the second unit, and the control unit integrates a first cumulative amount of electric power which is a cumulative value of the amount of electric power supplied to the heat source in the one-time puff action series, and the control unit notifies an end of the one-time puff action series when the first cumulative amount of electric power reaches the required amount of electric power.

A second feature according to the first feature is summarized as that the permissible amount of electric power is greater than two times of the required amount of electric power.

A third feature according to the first feature or the second feature is summarized as that the control unit notifies the end of the one-time puff action series by stopping a supply of electric power to the heat source.

A fourth feature according to the first feature or the second feature is summarized as that the control unit notifies the end of the one-time puff action series by a light-emitting mode of a light-emitting element.

A fifth feature according to the third feature is summarized as that the control unit integrates a second cumulative amount of electric power which is a cumulative value of the amount of electric power supplied to the heat source after attaching the second unit to the first unit, and when the second cumulative amount of electric power reaches the permissible amount of electric power, but the first cumulative amount of electric power does not reach the required amount of electric power, the control unit does not cut off the electric power source, and continues the supply of electric power to the heat source until the first cumulative amount of electric power reaches the required amount of electric power.

A sixth feature according to the fifth feature is summarized as that when the second cumulative amount of electric power reaches the permissible amount of electric power, the control unit notifies that the second unit must be replaced, by a light-emitting mode of a light-emitting element.

A seventh feature according to the fifth feature is summarized as that when the second cumulative amount of electric power reaches the permissible amount of electric power, and when the first cumulative amount of electric power reaches the required amount of electric power, the control unit notifies that the second unit must be replaced, by a light-emitting mode of a light-emitting element.

A eighth feature according to any one of the fifth feature to the seventh feature is summarized as that the control unit resets the first cumulative amount of electric power by a first operation, and resets the second cumulative amount of electric power by a second operation that is different from the first operation.

A ninth feature according to any one of the first feature to the eighth feature is summarized as that the permissible amount of electric power is determined in accordance with a life of the flavor source in a case where the second unit has the flavor source.

A tenth feature according to any one of the first feature to the ninth feature is summarized as that the permissible amount of electric power is determined in accordance with a life of the aerosol source in a case where the second unit has the aerosol source.

A eleventh feature according to any one of the first feature to the tenth feature is summarized as that the permissible amount of electric power is determined in accordance with a shorter life of a life of the flavor source and a life of the aerosol source in a case where the second unit has the flavor source and the aerosol source.

A twelfth feature is summarized as a computer-readable medium recorded a program used in a non-burning type flavor inhaler having a shape extending along a predetermined direction from a non-mouthpiece end toward a mouthpiece end, wherein the non-burning type flavor inhaler includes a first unit having the non-mouthpiece end, and a second unit attached to the first unit, the second unit includes an aerosol source generating aerosol or a flavor source, the non-burning type flavor inhaler includes a heat source configured to heat the aerosol source or the flavor source without burning, and a power source configured to supply electric power to the heat source, a permissible amount of electric power defined by a cumulative value of an amount of electric power that is permitted to be supplied to the heat source after attaching the second unit to the first unit is larger than a required amount of electric power defined by a cumulative value of an amount of electric power to be supplied to the heat source in a one-time puff action series which is a series of actions in which a puff action is repeated a predetermined number of times, the permissible amount of electric power is a condition for appropriately using the second unit, and the program causes a computer to execute a step of integrating a first cumulative amount of electric power which is a cumulative value of the amount of electric power supplied to the heat source in the one-time puff action series, the step of notifying an end of the one-time puff action series when the first cumulative amount of electric power reaches the required amount of electric power.

BRIEF DESCRIPTION OF THE DRAWINGS

FIG. 4 is a diagram showing an example of a light emitting mode according to the first embodiment.

FIG. 5 is a diagram showing an example of the light emitting mode according to the first embodiment.

DESCRIPTION OF THE EMBODIMENT

Figure 1:
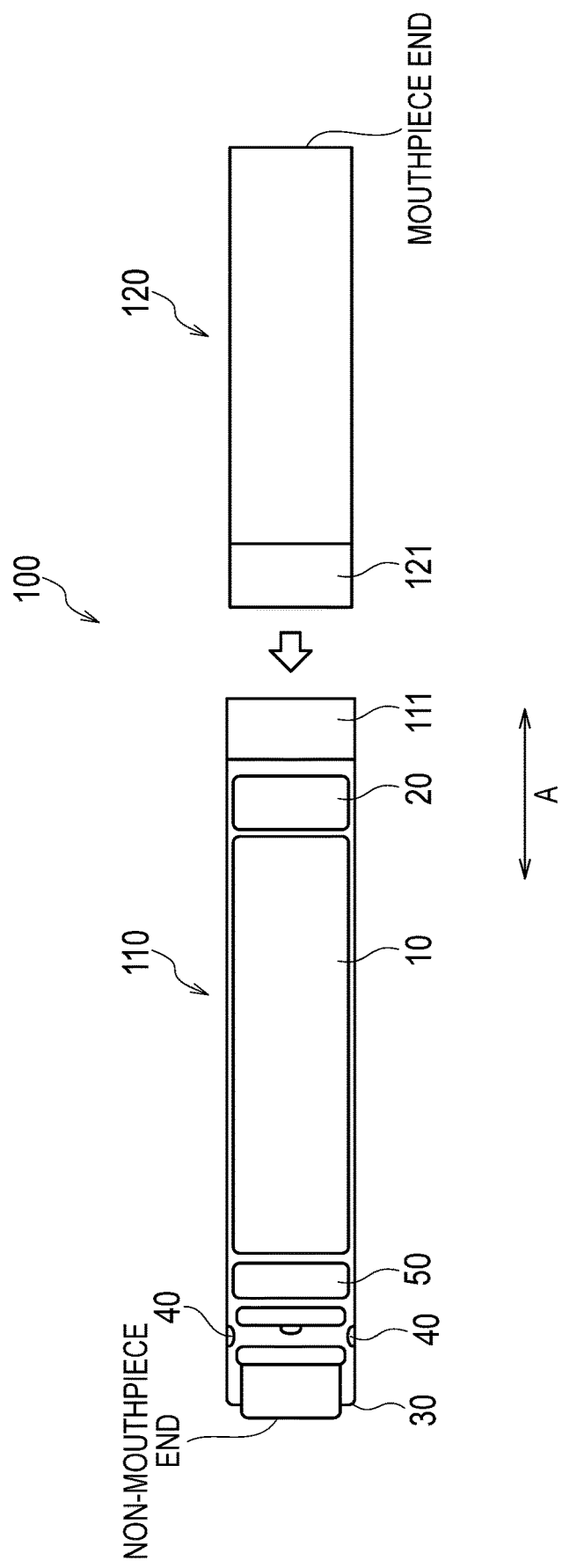
FIG. 1 is a diagram showing a non-burning type flavor inhaler 100 according to a first embodiment.

Hereinafter, the embodiments of the present invention will be described with reference to the drawings. In the following drawings, identical or similar components are denoted by identical or similar reference numerals. However, it should be noted that the drawings are schematic, and the ratio and the like of each of the dimensions is different from the reality.

Therefore, specific dimensions should be determined with reference to the description below. It is needless to mention that different relationships and ratio of dimensions may be included in different drawings.

OVERVIEW OF EMBODIMENT

The non-burning type flavor inhaler mentioned in background art is configured to automatically cut off the power source of the non-burning type flavor inhaler when the life of the aerosol source ends. It is noted that the life of the aerosol source is possible to be defined according to the permissible time (permissible amount of electric power), which is a cumulative value of the time (or the amount of electric power) during which the supply of electric power to the heat source is permitted after attaching the aerosol source as a condition for appropriately using the aerosol source.

Here, considering the replacement of the aerosol source in a one-time puff action series as a prerequisite, if the permissible time specified in the aerosol source is set to the same extent as the required time, which is the total of the time during which electric power is supplied to the heat source in a one-time puff action series, it is possible to know the end timing of the puff action series depending on the cut-off of the power source of the non-burning type flavor inhaler, and therefore, it is possible to use the non-burning type flavor inhaler with the similar sense of use as a regular cigarette. It is noted that a puff action series is a series of actions in which the puff action is repeated a predetermined number of times (for example, eight times).

However, if the permissible time specified in the aerosol source is longer than the required time, the power source of the non-burning type flavor inhaler does not cut off automatically even if it is time to end the one-time puff action series. Therefore, it is difficult for the user to understand the timing when the puff action series needs to be ended, with the similar sense of use as a regular cigarette.

The non-burning type flavor inhaler according to the Summary of Disclosure has a shape extending along a predetermined direction from a non-mouthpiece end toward a mouthpiece end. The non-burning type flavor inhaler includes a first unit having the non-mouthpiece end, a second unit that is attached to the first unit, and a control unit configured to control the non-burning type flavor inhaler. The second unit includes an aerosol source generating aerosol or a flavor source. The non-burning type flavor inhaler includes a heat source configured to heat the aerosol source or the flavor source without burning, and a power source configured to supply electric power to the heat source. The permissible amount of electric power defined by the cumulative value of the amount of electric power that is permitted to be supplied to the heat source after attaching the second unit to the first unit is larger than the required amount of electric power defined by a cumulative value of the amount of electric power to be supplied to the heat source in a one-time puff action series which is a series of actions in which the puff action is repeated a predetermined number of times. The permissible amount of electric power is a condition for appropriately using the second unit. The control unit integrates a first cumulative amount of electric power which is a cumulative value of the amount of electric power supplied to the heat source in the one-time puff action series, and the control unit notifies the end of the one-time puff action series when the first cumulative amount of electric power reaches the required amount of electric power.

In the overview of the embodiment, considering the fact that the permissible time specified in the second unit (for example, the flavor source or the aerosol source) is longer than the required time as a prerequisite, the control unit notifies the end of the one-time puff action series when the first cumulative amount of electric power reaches the required amount of electric power. As a result, even if the permissible time specified in the second unit (for example, the flavor source or the aerosol source) is longer than the required time, the user is capable of understanding the timing when the puff action series needs to be ended, with the similar sense of use as a regular cigarette.

First Embodiment

Non-Burning Type Flavor Inhaler

Figure 2:
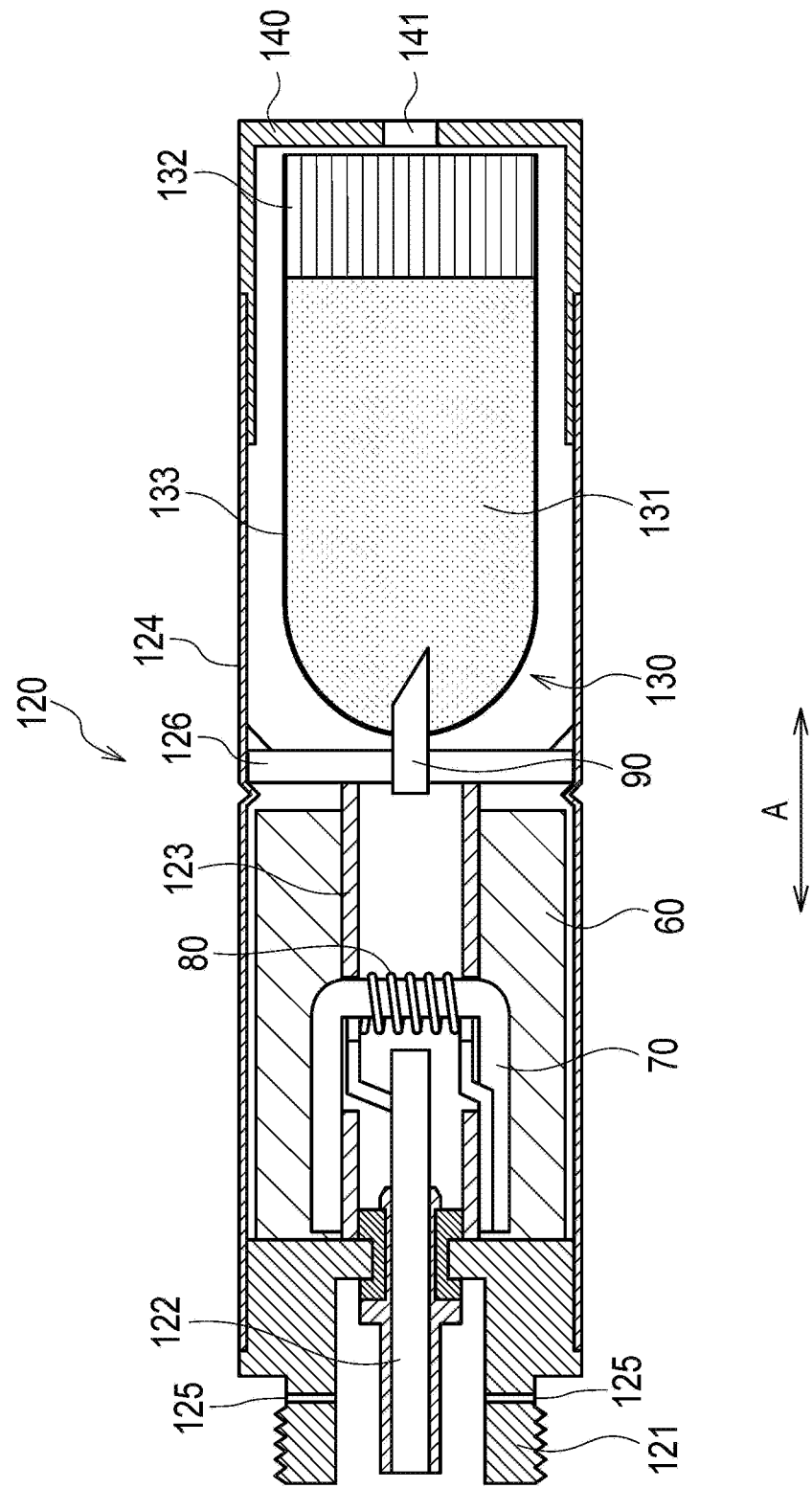
FIG. 2 is a diagram showing an atomization unit 120 according to the first embodiment.

A non-burning type flavor inhaler according to a first embodiment will be described, below. FIG. 1 is a diagram showing a non-burning type flavor inhaler 100 according to the first embodiment. FIG. 2 is a diagram showing an atomization unit 120 according to the first embodiment.

In the first embodiment, the non-burning type flavor inhaler 100 is a device for inhaling flavor without burning, and has a shape extending along a predetermined direction A from a non-mouthpiece end toward a mouthpiece end.

As shown in FIG. 1, the non-burning type flavor inhaler 100 has an electrical unit 110 and an atomization unit 120. The electrical unit 110 has a female connector 111 at a site adjacent to the atomization unit 120, and the atomization unit 120 has a male connector 121 at a site adjacent to the electrical unit 110. The female connector 111 has a spiral groove extending along a direction perpendicular to the predetermined direction A, and the male connector 121 has a spiral projection extending along a direction perpendicular to the predetermined direction A. As a result of mating of the female connector 111 and the male connector 121, the atomization unit 120 and the electrical unit 110 are connected. The atomization unit 120 is attached to the electrical unit 110 in a removable manner.

The electrical unit 110 has a power source 10, a sensor 20, a push button 30, a light-emitting element 40, and a control circuit 50.

The power source 10 is, for example, a lithium ion battery. The power source 10 supplies the electric power necessary for the operation of the non-burning type flavor inhaler 100. For example, the power source 10 supplies electric power to the sensor 20, the light-emitting element 40, and the control circuit 50. Further, the power source 10 supplies electric power to a heat source 80 described later.

The sensor 20 detects the wind pressure generated by the inhaling action of the user. Specifically, the sensor 20 detects the negative pressure generated when air is inhaled toward the atomization unit 120. Although not particularly restricted, the sensor 20 is configured by a piezoelectric element.

The push button 30 is configured to be pushed in the mouthpiece end side along the predetermined direction A. For example, when the push button 30 is pushed continuously over a predetermined number of times, the power source of the non-burning type flavor inhaler 100 is turned ON.

The light-emitting element 40 is, for example, a light source such as an LED or an electric lamp. The light-emitting element 40 is provided on a side wall extending along a predetermined direction. The light-emitting element 40 is preferably provided near the non-mouthpiece end. As a result, as compared to a case in which the light-emitting element is provided near the non-mouthpiece end on an axial line of the predetermined direction A, the user is capable of visually recognizing a light-emitting pattern of the light-emitting element 40 with ease, during the inhaling action. The light-emitting pattern of the light-emitting element 40 is a pattern by which a condition of the non-burning type flavor inhaler 100 is notified to the user.

The control circuit 50 controls the action of the non-burning type flavor inhaler 100. Specifically, the control circuit 50 controls the light-emitting pattern of the light-emitting element 40, and also controls the electric power supplied to the heat source 80.

As shown in FIG. 2, the atomization unit 120 has a holder 60, an absorber 70, the heat source 80, and a destruction portion 90. The atomization unit 120 has a capsule unit 130 and a mouthpiece unit 140. Here, the atomization unit 120 has the air lead-in hole 125 for taking in the outside air, an air flow path 122 communicated to the electrical unit 110 (sensor 20) via the male connector 121, and a ceramic 123 arranged in a cylindrical shape. The atomization unit 120 has a cylindrical outer wall 124 configured to form the outer shape of the atomization unit 120. The space enclosed by the ceramic 123 forms an air flow path. The ceramic 123, for example, includes alumina as the main constituent.

The holder 60 has a cylindrical shape, and holds an aerosol source configured to generate aerosol. The aerosol source is a liquid, such as glycerine or propylene glycol. The holder 60 is configured by a porous body which the aerosol source has been immersed, for example. The porous body is, for example, a resin web.

It is noted that in the first embodiment, the above-described ceramic 123 is arranged on the inner side of the holder 60, and the volatilization of the aerosol source held by the holder 60 is thus controlled.

The absorber 70 is provided adjacent to the holder 60, and is configured by a substance that sucks up the aerosol source from the holder 60. The absorber 70 is, for example, configured by a glass fiber.

The heat source 80 heats the aerosol source without burning. For example, the heat source 80 is a heating wire wound around the absorber 70. The heat source 80 heats the aerosol source that is sucked up by the absorber 70.

The destruction portion 90 is a member for destructing a part of a predetermined film 133 in a state in which the capsule unit 130 has been mounted. In the embodiment, the destruction portion 90 is held by a partition member 126 for separating the atomization unit 120 and the capsule unit 130. The partition member 126 is, for example, a polyacetal resin. The destruction portion 90 is, for example, a tubular hollow needle extending along the predetermined direction A. By piercing the tip of the hollow needle through the predetermined film 133, a part of the predetermined film 133 is destructed. Further, an air flow path that pneumatically communicates the atomization unit 120 and the capsule unit 130 is formed by the inner space of the hollow needle. Here, a mesh that has a roughness of an extent such that the raw material configuring a flavor source 131 does not pass through is preferably provided inside the hollow needle. The roughness of the mesh is, for example, 80 mesh or above and 200 mesh or below.

In such a case, the depth of penetration of the hollow needle inside the capsule unit 130 is preferably 1.0 mm or more and 5.0 mm or less, and more preferably 2.0 mm or more and 3.0 mm or less. As a result, since there is no destruction of sites other than the desired site of the predetermined film 133, it is possible to prevent the desorption of the flavor source 131 that is packed in the space partitioned by the predetermined film 133 and a filter 132. Further, since the detachment of the hollow needle from the concerned space is prevented, it is possible to favorably maintain the appropriate air flow path extending from the hollow needle to the filter 132.

In the vertical cross-section with respect to the predetermined direction A, the cross-sectional area of the vertical needle is preferably 2.0 mm$^2$ or more and 3.0 mm$^2$ or less. As a result, it is possible to prevent the dropping out of the flavor source 131 from the capsule unit 130 when the hollow needle is pulled out.

The tip of the hollow needle preferably has an inclination of 30° or more and 45° or less with respect to the vertical direction to the predetermined direction A.

However, the embodiment is not restricted thereto, and the destruction portion 90 may be a site adjacent to the predetermined film 133 in a state in which the capsule unit 130 has been mounted. A part of the predetermined film 133 may thus be destructed through the application of pressure to such a site by the user.

The capsule unit 130 is attached to a first unit in a removable manner. The capsule unit 130 has the flavor source 131, the filter 132, and the predetermined film 133. Further, the flavor source 131 is packed in the space partitioned by the predetermined film 133 and the filter 132. Here, the first unit is a unit configured by sites other than the capsule unit 130. For example, the first unit includes the above-described electrical unit 110, the holder 60, the absorber 70, and the heat source 80.

The flavor source 131 is provided at the mouthpiece end side from the holder 60 configured to hold the aerosol source, and generates a flavor that is inhaled by the user together with the aerosol generated from the aerosol source. Here, it must be noted that the flavor source 131 is configured by a solid substance so as not to flow out from inside the space partitioned by the predetermined film 133 and the filter 132. As the flavor source 131, it is possible to use shredded tobacco, a formed product obtained by forming the tobacco raw material in the shape of granules, and a formed product obtained by forming the tobacco raw material in the shape of a sheet. The flavor source 131 may be configured by a plant (for example, mint, herbs, etc.) other than tobacco. Flavorings, such as menthol, etc. may be added to the flavor source 131.

It is noted that when the flavor source 131 is configured by the tobacco raw material, the tobacco raw material is away from the heat source 80, and therefore, it is possible to inhale the flavor without heating the tobacco raw material. In other words, it must be noted that inhalation of unnecessary substances generated by heating of the tobacco raw material is controlled.

In the first embodiment, the amount of the flavor source 131 that is packed in the space partitioned by the filter 132 and the predetermined film 133 is preferably 0.15 g/cc or more and 1.00 g/cc or less. The occupancy rate of the volume occupied by the flavor source 131 in the space partitioned by the filter 132 and the predetermined film 133 is preferably 50% or more and 100% or less. It is noted that the capacity of the space partitioned by the filter 132 and the predetermined film 133 is preferably 0.6 mL or more and 1.5 mL or less. As a result, it is possible to store the flavor source 131 to an extent at which the user is capable of sufficiently tasting the flavor while retaining the capsule unit 130 at an appropriate size.

The air-flow resistance (pressure loss) of the capsule unit 130 in the case when air is inhaled at a flow rate of 1050 cc/min. from the tip portion (destructed portion) of the capsule unit 130 up to the end of the filter 132 in a state when a part of the predetermined film 133 is destructed by the destruction portion 90, and the atomization unit 120 and the capsule unit 130 are communicated is preferably 10 mmAq or more and 100 mmAq or less, and more preferably 20 mmAq or more and 90 mmAq or less, as a whole. By setting the air-flow resistance of the flavor source 131 within the above-described preferred range, the phenomenon of over-filtration of the aerosol by the flavor source 131 is controlled, and thus, it is possible to efficiently supply the flavor to the user. It is noted that since 1 mmAq is equivalent to 9.80665 Pa, the above-described air-flow resistance is possible to be expressed in Pa as well.

The filter 132 is adjacent to the mouthpiece end side with respect to the flavor source 131, and is configured by a substance having air permeability. The filter 132 is preferably, for example, an acetate filter. The filter 132 preferably has a roughness of an extent such that the raw material configuring the flavor source 131 does not pass through.

The air-flow resistance of the filter 132 is preferably 5 mmAq or more and 20 mmAq or less. As a result, it is possible to efficiently let the aerosol pass through while efficiently adsorbing the vapor component generated from the favor source 131, and thus, it is possible to supply an appropriate flavor to the user. Further, it is possible to offer the user the appropriate sense of resistance to air.

The ratio (mass ratio) of the mass of the flavor source 131 and the mass of the filter 132 is preferably in the range of 3:1 to 20:1, and more preferably in the range of 4:1 to 6:1.

The predetermined film 133 is integrally formed with the filter 132, and is configured by a member that does not have air permeability. Of the outer surface of the flavor source 131, the predetermined film 133 covers a portion excluding the portion adjacent to the filter 132. The predetermined film 133 includes at least one compound selected from a group configured by gelatin, polypropylene, and polyethylene terephthalate. Gelatin, polypropylene, polyethylene, and polyethylene terephthalate do not have air permeability, and are suitable for the formation of a thin film. Further, gelatin, polypropylene, polyethylene, and polyethylene terephthalate are able to acquire sufficient durability against the moisture contained in the flavor source 131. Polypropylene, polyethylene, and polyethylene terephthalate particularly have excellent water resistance. In addition, gelatin, polypropylene, and polyethylene have resistance to bases, and hence not tend to be degraded by the basic component even if the flavor source 131 has a basic component.

The predetermined film 133 preferably has a film thickness of 0.1 μm or more and 0.3 μm or less. As a result, it is possible to easily destruct a part of the predetermined film 133 while maintaining the function of protecting the flavor source 131 by the predetermined film 133.

As described above, the predetermined film 133 is integrally formed with the filter 132, however, the predetermined film 133, for example, is affixed on to the filter 132 by glue, or the like. Alternatively, the outer shape of the predetermined film 133 may be set to be smaller than the outer shape of the filter 132 in the vertical direction to the predetermined direction A so as to pack the filter 132 within the predetermined film 133, and fit the filter 132 within the predetermined film 133 by the restoring force of the filter 132. Else, an engagement portion for engaging the predetermined film 133 may be provided in the filter 132.

Here, although the shape of the predetermined film 133 is not particularly restricted, the predetermined film 133 preferably has a concave shape in the vertical cross-section with respect to the predetermined direction A. In such a case, after packing the flavor source 131 inside the predetermined film 133 having a concave shape, the opening of the predetermined film 133 in which the flavor source 131 is packed is closed by the filter 132.

When the predetermined film 133 has a concave shape in the vertical cross-section with respect to the predetermined direction A, of the cross-sectional area of the space enclosed by the predetermined film 133, the maximum cross-sectional area (that is, the cross-sectional area of the opening in which the filter 132 is fitted) is preferably 25 mm$^2$ or more and 80 mm$^2$ or less, and more preferably 25 mm$^2$ or more and 55 mm$^2$ or less. In such a case, the cross-sectional area of the filter 132 in the vertical cross-section with respect to the predetermined direction A is preferably 25 mm$^2$ or more and 55 mm$^2$ or less. The thickness of the filter 132 in the predetermined direction A is preferably 3.0 mm or more and 7.0 mm or less.

The mouthpiece unit 140 has a mouthpiece hole 141. The mouthpiece hole 141 is an opening configured to expose the filter 132. By inhaling aerosol from the mouthpiece hole 141, the user inhales the flavor together with the aerosol.

In the first embodiment, the mouthpiece unit 140 is configured in a removable manner with respect to the outer wall 124 of the atomization unit 120. For example, the mouthpiece unit 140 has a cup shape that is configured to fit in the inner surface of the outer wall 124. However, the embodiment is not limited thereto. The mouthpiece unit 140 may be attached to the outer wall 124 in a rotatable manner with the help of a hinge, etc.

In the first embodiment, the mouthpiece unit 140 is provided as a separate part from the capsule unit 130. That is, the mouthpiece unit 140 configures a part of the first unit. However, the embodiment is not limited thereto. The mouthpiece unit 140 may be integrally provided with the capsule unit 130. In such a case, it must be noted that the mouthpiece unit 140 configures a part of the capsule unit 130.

In the first embodiment, the electrical unit 110 and the atomization unit 120 configure the first unit having the non-mouthpiece end. On the other hand, the capsule unit 130 configures a second unit that is attached to the first unit. As described above, it must be noted that the capsule unit 130 has the flavor source 131.

(Life of Flavor Source)

It is possible to set the life of the above-described flavor source 131 as shown below, for example. Specifically, if the amount of supply of the flavor component (nicotine in the first embodiment) to the user immediately before starting the use of the non-burning type flavor inhaler 100 is 100%, it is possible to set that the life of the flavor source 131 has come to an end when the amount of supply becomes 50% or less as a result of use of the non-burning type flavor inhaler 100.

Alternatively, it is possible to set that the life of the flavor source 131 has come to an end if the amount of delivery of the flavor component that is supplied to the oral cavity of the user from the flavor source 131 falls below 20 μg when the inhaling action of the non-burning type flavor inhaler 100 is performed for 2.0 seconds at an inhalation rate of 27.5 mL/sec.

It is possible to increase or decrease the life of the flavor source 131 depending on factors such as the content of the flavor component (for example, nicotine) included in the tobacco raw material; existence of addition of a stabilizer (for example, a compound having characteristics, such as a distance of 17 or below between the solubility parameters with respect to the nicotine component, and a vapor pressure of 1 mmHg or below at 25° C., and specifically, a compound such as triethyl citrate, etc.), as well as type and amount of addition of the compound to be added; and a shape of the cartridge including the flavor source 131, particularly, a shape of the cartridge with which the amount of airflow to the flavor source 131 is controlled.

While it is possible to increase or decrease the life of the flavor source 131 by using the above-described method, it is preferable to adjust the composition of the flavor source 131 and the shape of the cartridge so that the amount of supply of the flavor component becomes 50% or less when the cumulative amount of electric power permitted at the time of supplying electric power to the atomization portion (heat source 80) is 50 J. Further, the cumulative amount of electric power until the amount of supply of the flavor component becomes 50% or less is more preferably 500 J or more, and is particularly preferred to be 1500 J or more. There is no particular restriction in the upper limit of the above-described cumulative amount of electric power, and for example, the upper limit can be set to 4000 J or less. In the non-burning type flavor inhaler 100 that satisfies a value of 500 J or above, which is the above-described preferable condition, for example, if the required amount of electric power is set to 100 J, it is possible to set the permissible amount of electric power to five times or more of the required amount of electric power. Similarly, for the non-burning type flavor inhaler 100 that satisfies a value of 1500 J or more, which is the above-described particularly preferred condition, it is possible to set the permissible amount of electric power to 10 times or more of the required amount of electric power.

(Life of Aerosol Source)

It is possible to set the life of the aerosol source as shown below, for example. Specifically, when the mass of the aerosol source falls below a threshold value of 5% at a mass standard with respect to the initial mass, that is, the mass immediately before the use of the non-burning type flavor inhaler 100, it is possible to set that the life of the aerosol source has come to an end. The threshold value is preferably 10%, and more preferably 20%.

Alternatively, when the mass of the aerosol source remaining in the non-burning type flavor inhaler 100 falls below a threshold value of 100 mg, it is possible to set that the life of the aerosol source has come to an end. The threshold value is more preferably 150 mg, and is particularly preferred to be 250 mg. By considering 100 mg, which is the preferable condition, as the threshold value, it is possible to more effectively reduce the damage occurring as a result of the heat discharged from the heat source 80 to the absorber 70 due to the depletion of the aerosol source. In addition, by considering 250 mg, which is the particularly preferable condition, as the threshold value, it is possible to notify the fact that the aerosol source needs to be replaced before the user perceives an attenuation in the amount of the aerosol.

It is possible to increase or decrease the life of the aerosol source depending on the amount of the aerosol source that the non-burning type flavor inhaler 100 is capable of retaining, but the amount of the aerosol source immediately before the non-burning type flavor inhaler 100 is operated, that is, the initial amount of the aerosol source is preferably 500 mg or more, and more preferably 1000 mg or more. There is no particular upper limit of the amount of the aerosol source since the amount is possible to be varied depending on the size of the space in which the aerosol source is held, but is preferably 3000 mg or less.

Alternatively, the cumulative amount of electric power until the residual amount of the aerosol source becomes 250 mg is preferably 2000 J to 5000 J, and more preferably 2000 J to 3000 J. With the non-burning type flavor inhaler 100 that has been adjusted to satisfy the preferable condition described above, for example, if the required amount of electric power is set to 100 J, it is possible to set the permissible amount of electric power to 20 times or more of the required amount of electric power.

(Control Circuit)

Figure 3:
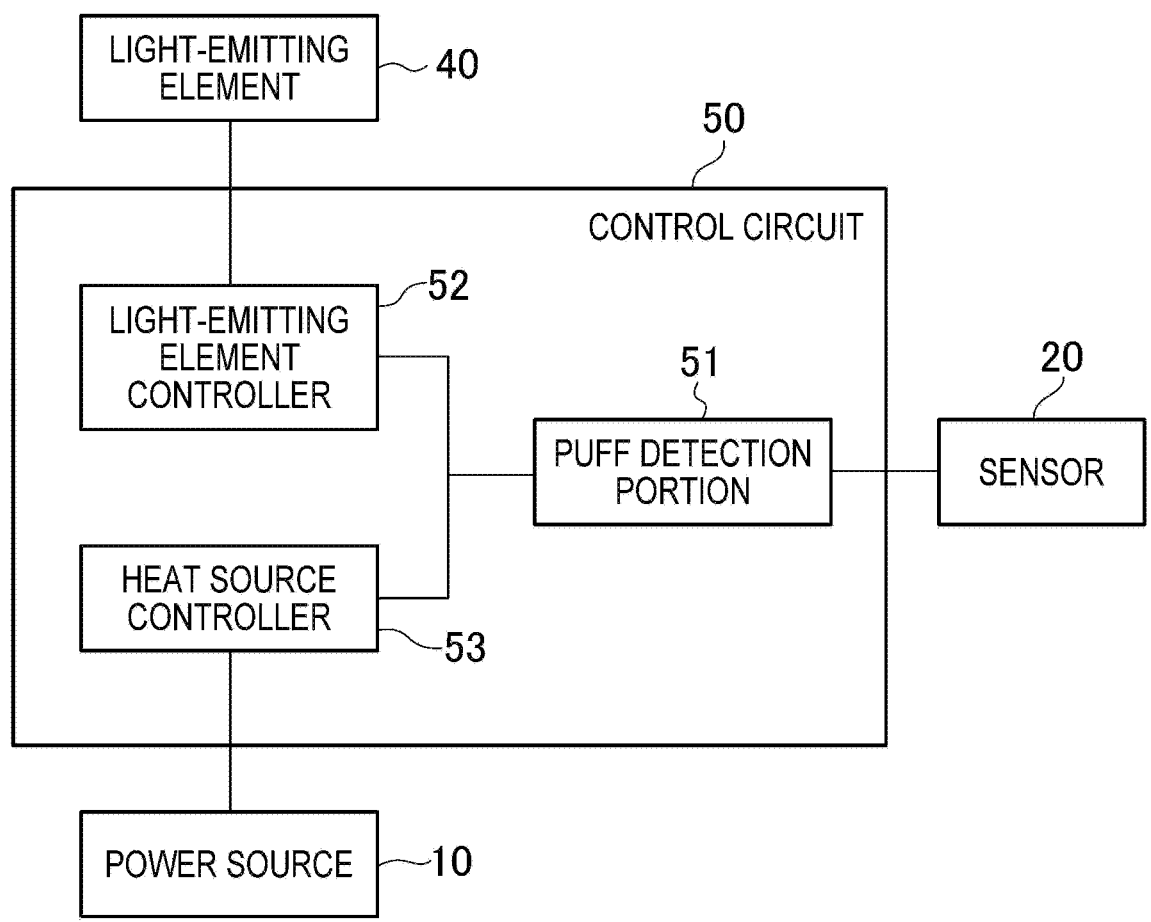
FIG. 3 is a block diagram showing a control circuit 50 according to the first embodiment.

A control circuit according to the first embodiment will be described, below. FIG. 3 is a block diagram showing the control circuit 50 according to the first embodiment.

As shown in FIG. 3, the control circuit 50 has a puff detection portion 51, a light-emitting element controller 52, and a heat source controller 53. The control circuit 50 is a control unit configured to control the non-burning type flavor inhaler 100, and is preferably provided in the electrical unit 110 (the first unit).

The puff detection portion 51 is connected to the sensor 20 configured to detect the wind pressure generated by the inhaling action of the user. The puff detection portion 51 detects the puffing state, on the basis of the detection result (for example, the negative pressure within the non-burning type flavor inhaler 100) of the sensor 20. In particular, the puff detection portion 51 detects a puffing state in which aerosol is inhaled, and a non-puffing state in which aerosol is not inhaled. As a result, the puff detection portion 51 is capable of specifying the number of times of the puff action of inhaling the aerosol. Further, the puff detection portion 51 is also capable of detecting a required time of a one-time puff action of inhaling the aerosol.

The light-emitting element controller 52 is connected to the light-emitting element 40 and the puff detection portion 51, and controls the light-emitting element 40. Specifically, the light-emitting element controller 52 controls the light-emitting element 40 according to a first light-emitting mode, in the puffing state in which aerosol is inhaled. On the other hand, the light-emitting element controller 52 controls the light-emitting element 40 according to a second light-emitting mode that is different from the first light-emitting mode, in the non-puffing state in which aerosol is not inhaled.

Here, the light-emitting mode is defined according to a combination of parameters such as the amount of light of the light-emitting element 40, the number of light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

In the first embodiment, the second light-emitting mode changes in accordance with the number of times of the puff action of inhaling aerosol. The first light-emitting mode may change in accordance with the number of times of the puff action of inhaling aerosol, or may be fixed regardless of the number of times of the puff action of inhaling aerosol.

For example, the first light-emitting mode is a mode in which a red-colored light-emitting element 40 is lit up in order to imitate the sense of use of a regular cigarette in which aerosol is generated in association with burning. The first light-emitting mode is preferably a mode in which the light-emitting element 40 is continuously lit up. Alternatively, the first light-emitting mode may be a mode in which lighting up of the light-emitting element 40 and lighting out of the light-emitting element 40 are repeated in a first cycle.

For example, the second light-emitting mode is a mode in which a blue-colored light-emitting element 40 is lit up in order to notify the user that the aerosol source is not heated up. The second light-emitting mode may be a mode in which lighting up of the light-emitting element 40 and lighting out of the light-emitting element 40 are repeated in a second cycle that is longer than the first cycle.

As described above, the second light-emitting mode changes in accordance with the number of times of the puff action of inhaling aerosol.

For example, the second light-emitting mode may be a mode in which the number of light-emitting elements 40 that are to be controlled increases with an increase in the number of times of the puff action. For example, the light-emitting element controller 52 controls one light-emitting element 40 by the second light-emitting mode in the first puff action, and controls two light-emitting elements 40 by the second light-emitting mode in the second puff action. Alternatively, the light-emitting element controller 52 controls n number of light-emitting elements 40 by the second light-emitting mode in the first puff action, and controls n−1 number of light-emitting elements 40 by the second light-emitting mode in the second puff action.

Alternatively, the second light-emitting mode may be a mode in which the amount of light of the light-emitting element 40 either increases or decreases with an increase in the number of times of the puff action. Else, the second light-emitting mode may be a mode in which the color of the light-emitting element 40 changes with an increase in the number of times of the puff action.

It is noted that even when the first light-emitting mode changes in accordance with the number of times of the puff action, the change in the first light-emitting mode is basically the same concept as the change in the second light-emitting mode.

In the first embodiment, when the number of times of the puff action of inhaling the aerosol reaches a predetermined number of times (for example, eight times), the light-emitting element controller 52 ends the control complying with the first light-emitting mode and the second light-emitting mode, and controls the light-emitting element 40 with an end light-emitting mode.

The end light-emitting mode is preferably different from the first light-emitting mode and the second light-emitting mode as long as the end light-emitting mode is a mode for notifying the user that it is time to end the puff action. For example, the end light-emitting mode is a mode in which the amount of light of the light-emitting element 40 is smaller than the first light-emitting mode and the second light-emitting mode, and the amount of light of the light-emitting element 40 reduces over time.

The heat source controller 53 is connected to the power source 10, and controls the amount of electric power supplied from the power source 10 to the heat source 80. It is noted that the amount of power is the result of multiplication of time and electric power (voltage or current), and is a value that is controlled by time and electric power. For example, the heat source controller 53 controls the voltage applied to the heat source 80 from the power source 10 by controlling the DC-DC converter, etc. that is arranged together with the power source 10.

Firstly, the heat source controller 53 gradually increases the amount of electric power supplied to the heat source 80 from the standard amount of electric power with an increase in the number of times of the puff action of inhaling the aerosol. As a result, it becomes possible to imitate the sense of use of a regular cigarette configured to generate aerosol in association with burning.

Here, the heat source controller 53 may control the power source 10 in such a way that when a puff action is performed after the number of times of the puff action exceeds the predetermined number of times, an amount of electric power that is smaller than the standard amount of electric power is supplied to the heat source 80. That is, the user may be notified about the end of a one-time puff action series by a reduction in the amount of electric power for the heat source 80. However, as described later, in the first embodiment, it is preferable to notify the user about the end of a one-time puff action series by stopping of the power supply to the heat source 80.

When a predetermined time period has elapsed after the number of times of the puff action exceeds a predetermined number of times, the heat source controller 53 turns OFF the power source of the non-burning type flavor inhaler 100. As a result, the waste of electric power of the non-burning type flavor inhaler 100 due to forgetting to turn off the power source of the non-burning type flavor inhaler 100 is controlled.

Here, the heat source controller 53 may combine the above-described actions to supply an amount of electric power that is smaller than the standard amount of electric power to the heat source 80 after the number of times of the puff action exceeds a predetermined number of times, and to turn OFF the power source of the non-burning type flavor inhaler 100 after the number of times of the puff action exceeds the predetermined number of times and when the non-puffing time period (the time period during which the puff action is not performed) passes a predetermined time.

The heat source controller 53 preferably increases the gradient of the amount of electric power supplied to the heat source 80 with an increase in the number of times of the puff action of inhaling the aerosol. Here, the gradient of the electric power is defined by the number of times of the puff action during which a fixed electric power is maintained, and the increment by which the electric power increases. That is, there is a reduction, with an increase in the number of times of the puff action, in the number of times of the puff action during which a fixed electric power is maintained. Alternatively, there is an increase, with an increase in the number of times of the puff action, in the increment by which the electric power increases. Alternatively, with an increase in the number of times of the puff action, there is a reduction in the number of times of the puff action during which a fixed electric power is maintained, and an increase in the increment by which the electric power increases.

In addition, the heat source controller 53 may control a first mode in which a first standard amount of electric power is used as the standard amount of electric power, and a second mode in which a second standard amount of electric power that is greater than the first standard amount of electric power is used as the standard amount of electric power. Three or more stages of the standard amount of electric power may be prepared as the standard amount of electric power. In such a case, the switching of the standard amount of electric power may be performed by an operation of the push button 30. For example, the first mode may be applied by pushing the push button 30 one time, and the second mode may be applied by pushing the push button 30 twice. Further, the push button 30 may be substituted by a touch sensor. The power source of the non-burning type flavor inhaler 100 may also be turned ON by performing the above-described operations. That is, turning ON of the power source and switching of the standard amount of electric power may be performed by a single action by operating the push button 30. However, the action of turning ON the power source by operating the push button 30 may be separated from the action of switching the standard amount of electric power.

Secondly, the heat source controller 53 controls a standard mode that must be applied to a user for whom the required time of a one-time puff action for inhaling aerosol is within the standard required time duration, and a shortened mode that must be applied to a user for whom the required time of a one-time puff action for inhaling aerosol is shorter than the standard required time duration. Here, the standard required time duration implies a time duration when the balance of the amount of supply of the aerosol (amount of TPM (Total Particulate Matter)) is particularly good.

Specifically, in a one-time puff action of the standard mode, the heat source controller 53 controls the power source 10 such that the standard amount of electric power is supplied to the heat source 80 for the duration until a first time period elapses, and controls the power source 10 such that an amount of electric power that is smaller than the standard amount of electric power is supplied to the heat source 80 for the duration after the first time period has elapsed. It is noted that for the duration after the first time period has elapsed, the heat source controller 53 may immediately set the amount of electric power supplied to the heat source 80 to zero, or may reduce the amount of electric power supplied to the heat source 80 over time.

Here, the first time period is preferably same as the end timing of the above-described standard required time duration. However, the first time period may be longer than the end timing of the standard required time duration within a range in which the balance of the amount of supply of the aerosol (the TPM amount) is permitted.

On the other hand, in a one-time puff action of the shortened mode, the heat source controller 53 controls the power source 10 such that a first amount of electric power that is greater than the standard amount of electric power is supplied to the heat source 80 for the duration until a second time period elapses, and controls the power source 10 such that a second amount of electric power that is smaller than the first amount of electric power is supplied to the heat source 80 for the duration until a third time period after the second time period elapses, and also controls the power source 10 such that an amount of electric power that is smaller than the second amount of electric power is supplied to the heat source 80 for the duration after the third time period has elapsed. It is noted that for the duration after the third time period has elapsed, the heat source controller 53 may immediately set the amount of electric power supplied to the heat source 80 to zero, or may reduce the amount of electric power supplied to the heat source 80 over time.

Here, the second time period is preferably shorter than the start timing of the above-described standard required time duration. However, the second time period may be included in the standard required time duration, or may be longer than the end timing of the standard required time duration. The third time period is preferably same as the end timing of the above-described standard required time duration. However, the third time period may be longer than the end timing of the standard required time duration within a range in which the balance of the amount of supply of the aerosol (the TPM amount) is permitted.

Further, the second amount of electric power that is smaller than the first amount of electric power may be the same as the above-described standard amount of electric power. However, the second amount of electric power may be greater than the standard amount of electric power, or may be smaller than the standard amount of electric power.

It is noted that as described above, the heat source controller 53 gradually increases the amount of electric power supplied to the heat source 80 from the standard amount of electric power with an increase in the number of times of the puff action. In other words, it must be noted that the standard amount of electric power in a one-time puff action is synonymous with the standard amount of electric power described above, and increases with an increase in the number of times of the puff action.

The heat source controller 53 may set the standard mode or the shortened mode depending on the learning of the puff action by the user. In particular, when the required time of a one-time puff action that is acquired by learning is within the standard required time duration, the heat source controller 53 sets the standard mode. When the required time of a one-time puff action that is acquired by learning is shorter than the standard required time duration, the heat source controller 53 sets the shortened mode.

In the first embodiment, the atomization unit 120 is removable with respect to the electrical unit 110. Further, the capsule unit 130 is removable with respect to the first unit including the electrical unit 110. In other words, it is possible to reuse the electrical unit 110 over a plurality of times of puff action series. A puff action series is a series of actions in which the puff action is repeated a predetermined number of times. Therefore, by learning the required time of a one-time puff action in the first puff action series, the standard mode or the shortened mode may be set in the second puff action series or thereafter. Alternatively, by learning the required time of a one-time puff action in the first n-time puff actions in a one-time puff action series, the standard mode or the shortened mode may be set for the n+1 (or, n+2)th puff action or thereafter.

Alternatively, the heat source controller 53 may set the standard mode or the shortened mode depending on the operation by the user. In such a case, a switch for switching the standard mode and the shortened mode is provided in the non-burning type flavor inhaler 100. It is noted that the switching of the standard mode and the shortened mode may be permitted in a one-time puff action series. Alternatively, the mode that is set initially may be applied in a fixed manner without permitting the switching of the standard mode and the shortened mode in a one-time puff action series.

(Light-Emitting Mode)

An example of a light-emitting mode according to the first embodiment will be described, below. FIG. 4 and FIG. 5 are diagrams showing an example of the light emitting mode according to the first embodiment. FIG. 4 and FIG. 5 illustrate a case in which the user must end a puff action series, in principle, when the number of times of the puff action reaches eight times (predetermined number of times).

Firstly, a first example of the light-emitting mode will be described with reference to FIG. 4. As shown in FIG. 4, a first light-emitting pattern in the puffing state is fixed regardless of the number of times of the puff action. On the other hand, a second light-emitting pattern in the non-puffing state changes in accordance with the number of times of the puff action.

For example, as shown in FIG. 4, in a non-puffing state #1 to a non-puffing state #4, a light-emitting mode #2-1 is used as the second light-emitting mode. In a non-puffing state #5 to a non-puffing state #7, a light-emitting mode #2-2 is used as the second light-emitting mode. In a non-puffing state #8, a light-emitting mode #2-3 is used as the second light-emitting mode. It is noted that in the ninth non-puffing state and thereafter, the above-described end light-emitting mode is used.

On the other hand, in a puffing state #1 to a puffing state #8, a light-emitting mode #1 is used as the first light-emitting mode. Even in the ninth puffing state and thereafter, the light-emitting mode #1 may be used as the first light-emitting mode, or a light-emitting mode different from the first light-emitting mode and the second light-emitting mode may be used in order to indicate that the puff is in excess of eight times (predetermined number of times).

The light-emitting mode #1, the light-emitting mode #2-1, the light-emitting mode #2-2, the light-emitting mode #2-3, and the end light-emitting mode are different light-emitting modes to each other. As described above, the light-emitting mode is defined according to a combination of parameters such as the amount of light of the light-emitting element 40, the number of the light-emitting elements 40 that are in the lit-up state, the color of the light-emitting element 40, the cycle of repetition of lighting up of the light-emitting element 40 and lighting out of the light-emitting element 40, etc. A different light-emitting mode implies a light-emitting mode in which any one of the above-described parameters is different.

For example, the light-emitting mode #1 is preferably a light-emitting mode that offers an image of burning in order to imitate the sense of use of a regular cigarette in which aerosol is generated in association with burning. The light-emitting mode #2-1 is a light-emitting mode that offers an image of an initial stage of the puff action series, the light-emitting mode #2-2 is a light-emitting mode that offers an image of a middle stage of the puff action series, and the light-emitting mode #2-3 is a light-emitting mode that offers an image of an end stage of the puff action series. The end light-emitting mode is preferably a mode for notifying the user that it is time to end the puff action.

Secondly, the first example of the light-emitting mode will be described with reference to FIG. 5. As shown in FIG. 5, both the first light-emitting pattern in the puffing state and the second light-emitting pattern in the non-puffing state change in accordance with the number of times of the puff action.

For example, as shown in FIG. 5, in the non-puffing state, the light-emitting mode #2-1, the light-emitting mode #2-2, and the light-emitting mode #2-3 are used as the second light-emitting mode, in a similar manner of the case shown in FIG. 4.

On the other hand, in the puffing state #1 to the puffing state #4, a light-emitting mode #1-1 is used as the first light-emitting mode. In a puffing state #5 to a puffing state #7, a light-emitting mode #1-2 is used as the first light-emitting mode. In a puffing state #8, a light-emitting mode #1-3 is used as the first light-emitting mode. It is noted that in the ninth puffing state and thereafter, a light-emitting mode #1-4 is used.

It is preferable that the light-emitting mode #1-1 is a light-emitting mode that offers an image of an initial stage of the puff action series, the light-emitting mode #1-2 is a light-emitting mode that offers an image of a middle stage of the puff action series, and the light-emitting mode #1-3 is a light-emitting mode that offers an image of an end stage of the puff action series. It is noted that, similarly to the end light-emitting mode, the light-emitting mode #1-4 is preferably a mode for notifying the user that it is time to end the puff action.

As shown in FIG. 4 and FIG. 5, the first embodiment illustrates a case in which the light-emitting mode in the non-puffing state #1 (that is, the non-puffing state immediately after turning ON the power source of the non-burning type flavor inhaler 100) is the second light-emitting mode (light-emitting mode #2-1). However, the embodiment is not limited thereto. The light-emitting mode in the non-puffing state #1 may be a start light-emitting mode that is different from the second light-emitting mode. The start light-emitting mode is preferably a mode for notifying the user that preparations have been made to start the puff action.

(Power Control in Puff Action Series)

Figure 6:
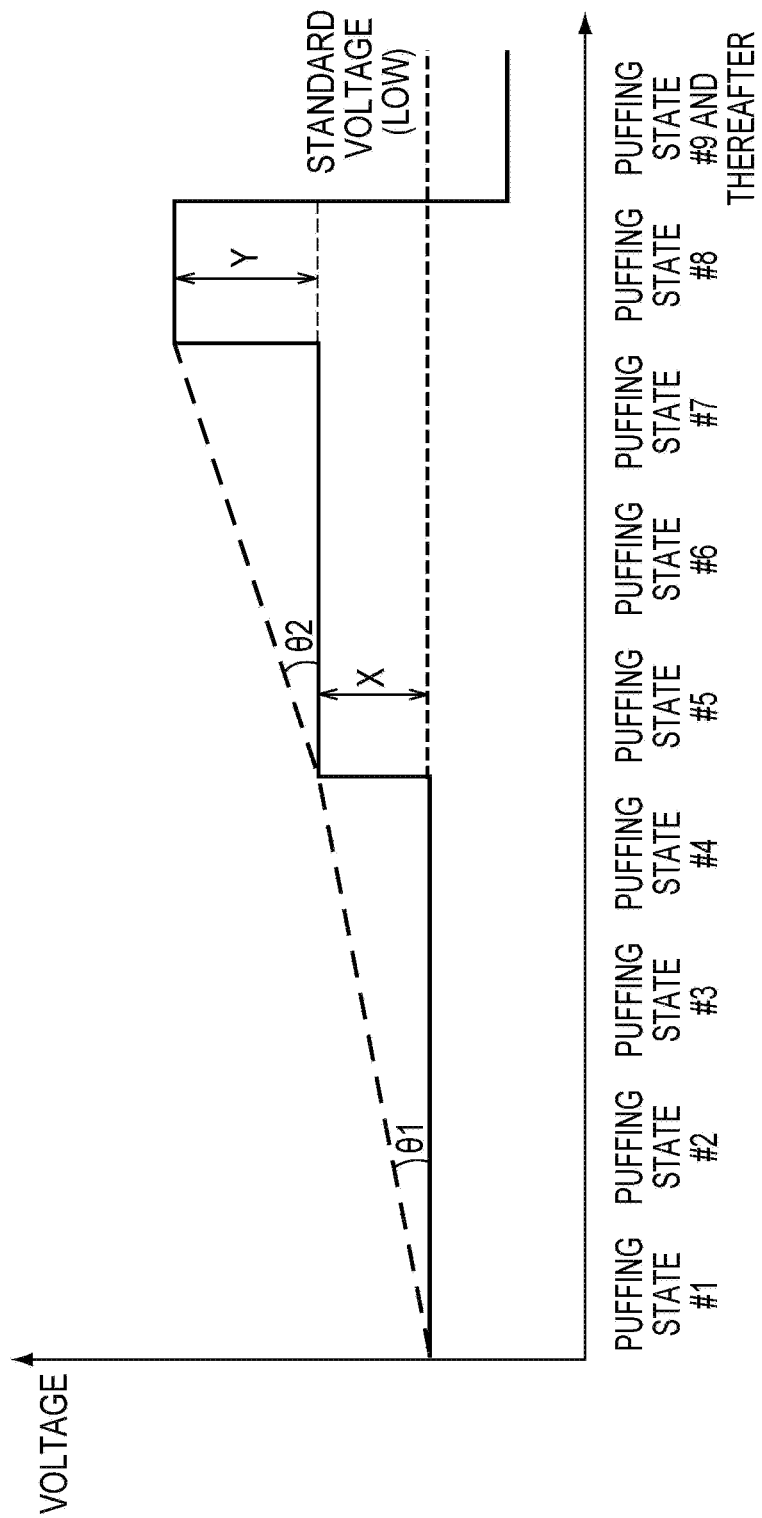
FIG. 6 is a diagram showing an example of power control in a puff action series according to the first embodiment.
Figure 7:
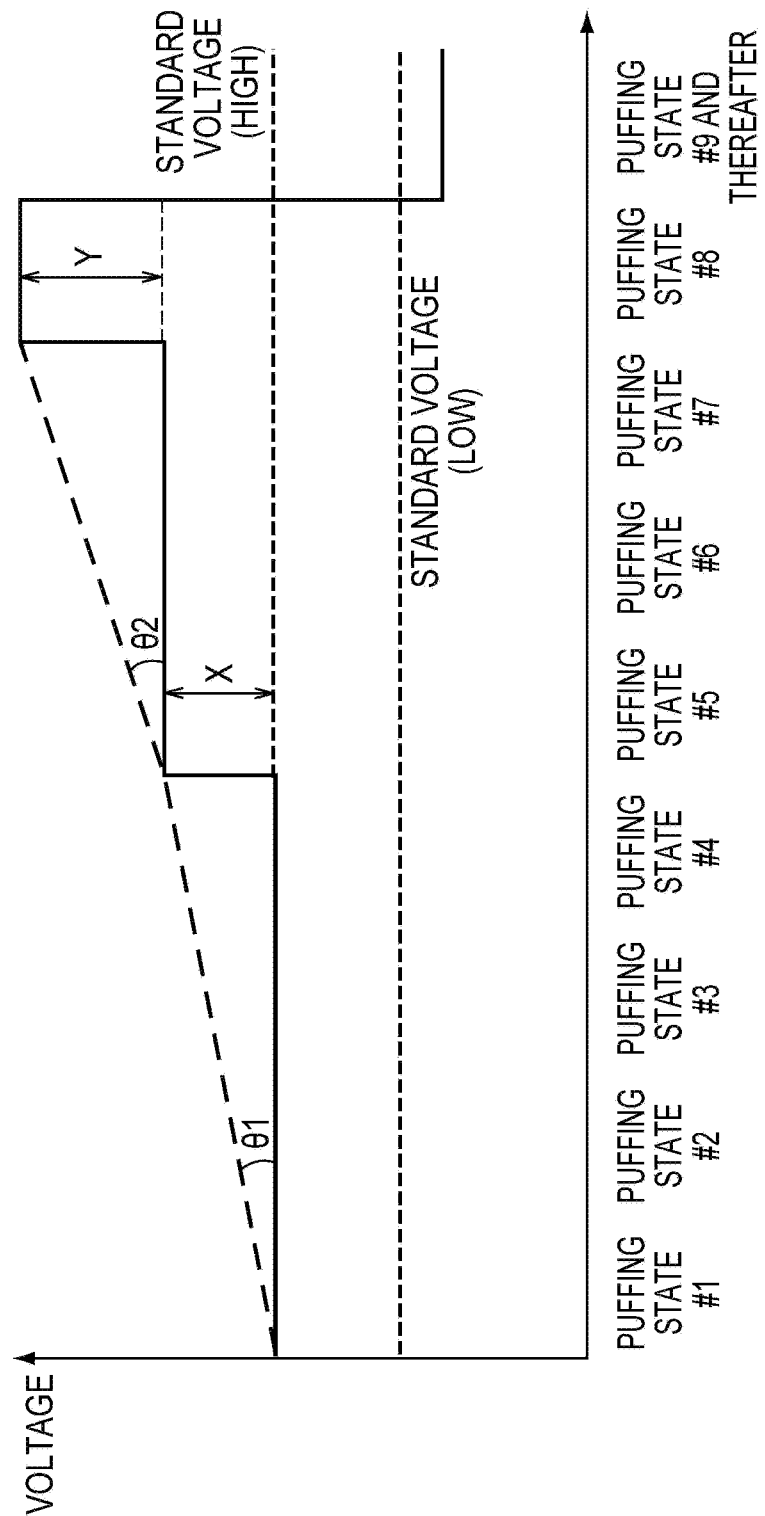
FIG. 7 is a diagram showing an example of power control in the puff action series according to the first embodiment.

An example of power control in a puff action series according to the first embodiment will be described, below. FIG. 6 and FIG. 7 are diagrams showing an example of power control in the puff action series according to the first embodiment. FIG. 6 and FIG. 7 illustrate a case in which the user must end a puff action series, in principle, when the number of times of the puff action reaches eight times (a predetermined number of times). Further, it must be noted that the behavior of the supplied electric power in the non-puffing state is omitted in FIG. 6 and FIG. 7 since electric power is not supplied to the heat source 80 in the non-puffing state.

Here, a case in which the amount of electric power supplied to the heat source 80 is controlled depending on the voltage applied to the heat source 80 will be illustrated. Therefore, in the first embodiment, it may be assumed that the amount of electric power is synonymous with voltage. Further, FIG. 6 shows the first mode (Low mode) in which a first voltage is used as the standard voltage, and FIG. 7 shows a second mode (High mode) in which a second voltage that is higher than the first voltage is used as the standard voltage. It is noted that the standard voltage is different, but the behavior of the voltage applied to the heat source 80 is similar in the first mode (Low mode) and the second mode (High mode).

As shown in FIG. 6 and FIG. 7, the heat source controller 53 gradually increases the voltage applied to the heat source 80 from the standard voltage with an increase in the number of times of the puff action of inhaling the aerosol. Specifically, in the puffing state #1 to the puffing state #4, the voltage applied to the heat source 80 is fixed, and the standard voltage is applied to the heat source 80. In the puffing state #5 to the puffing state #7, the voltage applied to the heat source 80 is fixed, and a voltage that is one step larger than the standard voltage is applied to the heat source 80. In the puffing state #8, a voltage that is two steps larger than the standard voltage is applied to the heat source 80. In the ninth puffing state and thereafter, a voltage that is smaller than the standard voltage is applied to the heat source 80.

As described above, the heat source controller 53 increases the gradient of the voltage applied to the heat source 80 with an increase in the number of times of the puff action of inhaling the aerosol.

For example, there is a reduction, with an increase in the number of times of the puff action, in the number of times of the puff action during which a fixed voltage is maintained. That is, the number of times of the puff action during which the standard voltage is applied is four, the number of times of the puff action during which a voltage that is one step larger than the standard voltage is applied is three, and the number of times of the puff action during which a voltage that is two steps larger than the standard voltage is applied is one. Alternatively, there is a reduction, with an increase in the number of times of the puff action, in the number of times of the puff action during which a fixed voltage is maintained. Alternatively, an increment Y of the voltage at the second time is larger than an increment X of the voltage of the first step.

As a result, there is an increase, with an increase in the number of times of the puff action, in the gradients ($\theta 1$ and $\theta 2$) of the voltage defined by the number of times of the puff action during which a fixed voltage is maintained, and the increment by which the voltage increases. In other words, the gradient $\theta 2$ of the middle stage of the puff action series is larger than the gradient $\theta 1$ of the initial stage of the puff action series.

In FIG. 6 and FIG. 7, the number of steps in which the voltage applied to the heat source 80 increases is two; however, the embodiment is not limited thereto. The number of steps in which the voltage applied to the heat source 80 increases may be three or more. Alternatively, the number of steps in which the voltage applied to the heat source 80 increases may be one.

(Power Control in One-Time Puff Action)

Figure 8:
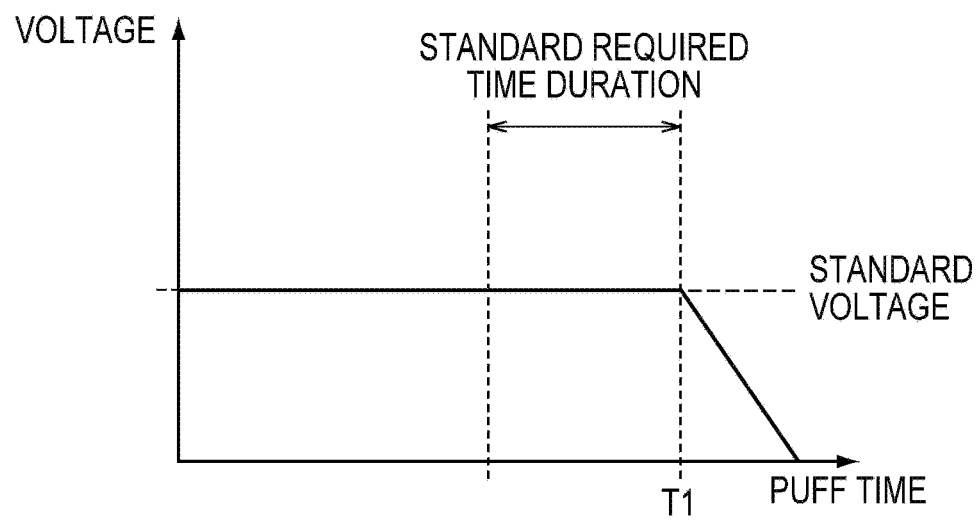
FIG. 8 is a diagram showing an example of power control in a one-time puff action according to the first embodiment.
Figure 9:
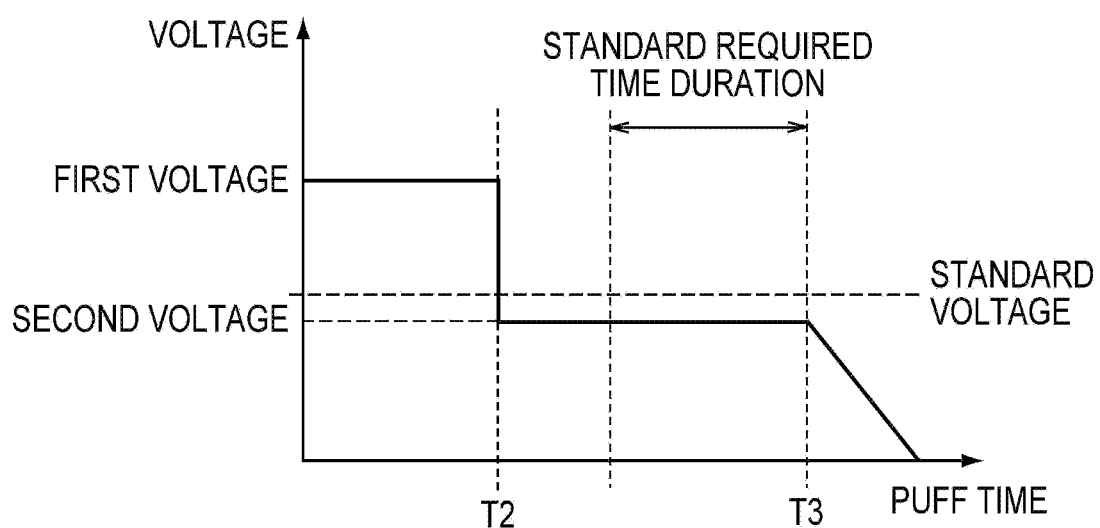
FIG. 9 is a diagram showing an example of power control in the one-time puff action according to the first embodiment.

An example of power control in a one-time puff action according to the first embodiment will be described, below. FIG. 8 and FIG. 9 are diagrams showing an example of power control in a one-time puff action according to the first embodiment. FIG. 8 and FIG. 9 illustrate a case in which the user must end a puff action series, in principle, when the number of times of the puff action reaches eight times (predetermined number of times).

Here, a case in which the amount of electric power supplied to the heat source 80 is controlled depending on the voltage applied to the heat source 80 will be illustrated. Therefore, in the first embodiment, it may be assumed that the amount of electric power is synonymous with voltage. Further, FIG. 8 shows a behavior of the voltage that is applied to the heat source 80 in the standard mode, and FIG. 9 shows a behavior of the voltage that is applied to the heat source 80 in the shortened mode.

As shown in FIG. 8, in the standard mode, the standard voltage is applied to the heat source 80 for the duration until a first time period T1 elapses. A voltage smaller than the standard voltage is applied to the heat source 80 for the duration after the first time period T1 has elapsed.

Here, a case is illustrated in which the first time period T1 is the same as the end timing of the standard required time duration. However, as described above, the first time period T1 is not limited thereto.

As shown in FIG. 9, in the shortened mode, a first voltage that is larger than the standard voltage is applied to the heat source 80 for the duration until a second time period T2 elapses. A second voltage that is smaller than the first voltage is applied to the heat source 80 for the duration until a third time period T3 after the second time period T2 elapses. A voltage smaller than the second voltage is applied to the heat source 80 for the duration after the third time period T3 has elapsed.

Here, a case is illustrated in which the second time period is shorter than the start timing of the standard required time duration. A case is illustrated in which the third time period is same as the end timing of the standard required time duration. A case is illustrated in which the second voltage is smaller than the standard voltage. However, as described above, the second time period T2, the third time period T3, and the second voltage are not limited thereto.

It is noted that a change in the required time of a one-time puff action is expected when the standard mode or the shortened mode has been set. Even in such a case, it must be noted that the voltage becomes zero at the same timing of the end of the puff action by tracing the profile of the voltage shown in FIG. 8 or FIG. 9. In other words, it must be noted that complex control such as continuous control of the amount of supply of the electric power on the basis of the air flow (inhalation rate) is not necessary during the time when electric power is being supplied to the heat source 80, since it may be favorable to control the amount of electric power supplied to the heat source according to the predetermined action mode.

(Startup/End Process)

A startup/end process according to the first embodiment will be described, below. Specifically, the above-described control circuit 50 controls the non-burning type flavor inhaler 100, and executes the process described below.

It is noted that in the first embodiment, the permissible amount of electric power, which is a cumulative value of the amount of electric power that is permitted to be supplied to the heat source 80 after attaching the second unit (here, the capsule unit 130) to the first unit (here, the electrical unit 110 and the atomization unit 120), is larger than the required amount of electric power, which is a cumulative value of the amount of electric power to be supplied to the heat source 80 in a one-time puff action series, which is a series of actions in which the puff action is repeated a predetermined number of times. The amount of electric power is the result of multiplication of time and electric power (voltage or current), and is a value that is controlled by time and electric power. Although there is no particular restriction in the specific numeric value of the required amount of electric power, the required amount of electric power, for example, is preferably the amount of electric power corresponding to the TPM amount equivalent to one regular cigarette under the standard smoking apparatus conditions stipulated according to ISO. Alternatively, the required amount of electric power is preferably selected from the range of 50 J to 200 J, and more preferably selected from the range of 50 J to 100 J. Further, the upper-limit value of the required amount of electric power is preferably ½ or less of the permissible amount of electric power, more preferably ⅕ or less, and is particularly preferred to be ¹⁄₁₀ or less of the permissible amount of electric power. It is noted that the required amount of power may be a value that is set beforehand, or may be a value that is set arbitrarily by the user.

Further, the permissible amount of electric power is a condition for appropriately using the second unit. That is, in the first embodiment, the permissible amount of electric power is a condition for the flavor source 131 contained in the capsule unit 130 to be appropriately generated. The permissible amount of electric power is specified in accordance with the life of the flavor source 131. In addition, the permissible amount of electric power is preferably greater than two times of the required amount of electric power.

Under such a prerequisite, the control circuit 50 integrates a first cumulative amount of electric power, which is a cumulative value of the amount of electric power supplied to the heat source 80 in a one-time puff action series, and notifies the end of the one-time puff action series when the first cumulative amount of electric power reaches the required amount of electric power. Here, the control circuit 50 may notify the end of the one-time puff action series by stopping of the supply of electric power to the heat source 80. At the time when the first cumulative amount of electric power reaches the required amount of electric power, the supply of electric power to the heat source 80 may be stopped, or the power source 10 of the non-burning type flavor inhaler 100 may be cut off. Alternatively, when the first cumulative amount of electric power reaches the required amount of electric power, the end of a one-time puff action series may be notified by the light-emitting mode of the light-emitting element 40, after which the end of the one-time puff action series may be again notified by stopping the supply of electric power to the heat source 80 at the time when the power source 10 of the non-burning type flavor inhaler 100 is cut off. Alternatively, when the first cumulative amount of electric power reaches the required amount of electric power, the end of the one-time puff action series may be notified by stopping the supply of electric power to the heat source 80 and the light-emitting mode of the light-emitting element 40, after which the power source 10 of the non-burning type flavor inhaler 100 may be cut off. Alternatively, the control circuit 50 may notify the end of the one-time puff action series by the light-emitting mode of the light-emitting element 40. Else, the control circuit 50 may notify the end of the one-time puff action series by both the stopping of the supply of electric power to the heat source 80 and the light-emitting mode of the light-emitting element 40.

In the first embodiment, the control circuit 50 preferably integrates a second cumulative amount of electric power, which is a cumulative value of the amount of electric power that is supplied to the heat source 80, after attaching the second unit (here, the capsule unit 130) to the first unit (here, the electrical unit 110 and the atomization unit 120). In such a case, if the second cumulative amount of electric power reaches the permissible amount of electric power, but the first cumulative amount of electric power does not reach the required amount of electric power, the control circuit 50 preferably does not cut off the power source 10, and continues the supply of electric power to the heat source 80 until the first cumulative amount of electric power reaches the required amount of electric power.

In the first embodiment, when the second cumulative amount of electric power reaches the permissible amount of electric power, and the first cumulative amount of electric power reaches the required amount of electric power, the control circuit 50 preferably notifies that the second unit must be replaced, by the light-emitting mode of the light-emitting element 40.

In the first embodiment, the control circuit 50 preferably resets the first cumulative amount of electric power by a first operation, and resets the second cumulative amount of electric power by a second operation that is different from the first operation. Here, the first operation is an operation that is performed for starting the second puff action series and thereafter, from among a plurality of times of puff action series executed after attaching the second unit (here, the capsule unit 130) to the first unit (here, the electrical unit 110 and the atomization unit 120). The second operation is an operation that is performed for starting the puff action series of the first time, from among the plurality of times of puff action series executed after attaching the second unit (here, the capsule unit 130) to the first unit (here, the electrical unit 110 and the atomization unit 120).

It is noted that the first cumulative amount of electric power is preferably reset by the second operation. However, when a detection means configured to detect the replacement of the second unit (here, the capsule unit 130) is provided in the first unit, the first cumulative amount of electric power may be reset automatically by the detection of replacement of the second unit (here, the capsule unit 130). In such a case, it must be noted that the first cumulative amount of electric power need not be reset by the second operation.

Next, an operation of the above-described control circuit 50 will be described with reference to a flowchart. FIG. 10 to FIG. 14 are flowcharts showing the startup/end process according to the first embodiment.

It is noted that as described above, the amount of electric power is the result of multiplication of time and electric power (voltage or current), and is a value that is controlled by time and electric power. Hereinafter, the permissible amount of electric power, the required amount of electric power, the first cumulative amount of electric power, and the second cumulative amount of electric power will be described as values that are managed only by time, by assuming that the electric power (voltage or current) is fixed. That is, the permissible amount of electric power is replaced by a permissible time threshold value, and the required amount of electric power is replaced by a required time threshold value. The first cumulative amount of electric power is replaced by a first cumulative time period (hereinafter, Tc), and the second cumulative amount of electric power is replaced by a second cumulative time period (hereinafter, Ta).

In particular, the permissible time threshold value is a cumulative value of the time period during which the supply of electric power to the heat source 80 after attaching the second unit to the first unit is permitted. The required time threshold value is a cumulative value of the time period during which electric power must be supplied to the heat source 80 in a one-time puff action series. The second cumulative time period (Ta) is a cumulative value of the time period during which electric power is supplied to the heat source 80 after attaching the second unit to the first unit. That is, the second cumulative time period (Ta) may be considered as a cumulative value of the time period during which the puffing state is occurred after attaching the second unit to the first unit. The first cumulative time period (Tc) is a cumulative value of the time period during which electric power is supplied to the heat source 80 in a one-time puff action series. That is, the first cumulative time period (Tc) may be considered as a cumulative value of the time period during which the puffing state is occurred in a one-time puff action series.

Figure 10:
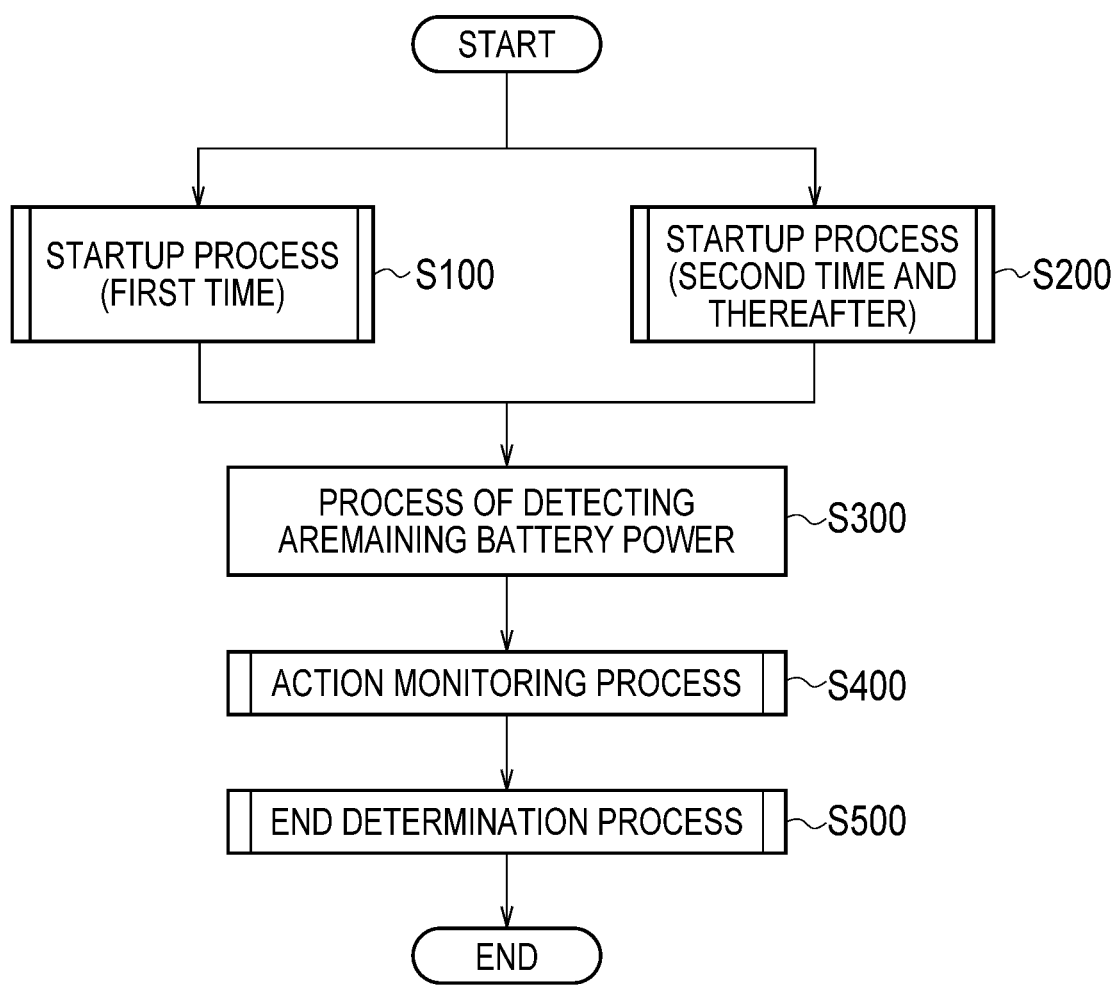
FIG. 10 is a flowchart showing a startup/end process according to the first embodiment.

As shown in FIG. 10, in step S100, the control circuit 50 executes a startup process (first time). The startup process (first time) is a process that is performed when starting the puff action series of the first time, from among the plurality of times of puff action series executed after attaching the second unit (here, the capsule unit 130) to the first unit (here, the electrical unit 110 and the atomization unit 120). It is noted that the startup process (first time) will be described in detail later (see FIG. 11).

In step S200, the control circuit 50 executes a startup process (second time and thereafter). The startup process (second time and thereafter) is a process that is performed when starting the puff action series of the second time and thereafter, from among the plurality of times of puff action series executed after attaching the second unit (here, the capsule unit 130) to the first unit (here, the electrical unit 110 and the atomization unit 120). It is noted that the startup process (second time and thereafter) will be described in detail later (see FIG. 12).

In step S300, the control circuit 50 executes a process of detecting the remaining battery power. Specifically, if the voltage of the power source 10 is less than a predetermined threshold value, the control circuit 50 cuts off the power source 10 after notifying, through the emitted light (for example, blinking of the LED in red color for three seconds) of the light-emitting element 40, that the power source 10 needs to be replaced or charged through. On the other hand, if the voltage of the power source 10 is equal to or more than the predetermined threshold value, the control circuit 50 moves to a process of step S400.

It is noted that in step S300, the above-described action mode (standard mode or shortened mode) may be decided.

In step S400, the control circuit 50 executes an action monitoring process. The action monitoring process is a process in which each puff action is monitored in a one-time puff action series. It is noted that the action monitoring process will be described in detail later (see FIG. 13).

In step S500, the control circuit 50 executes an end determination process. The end determination process is a process of determining the end of a one-time puff action series. It is noted that the end determination process will be described in detail later (see FIG. 14).

(Startup Process (First Time))

Figure 11:
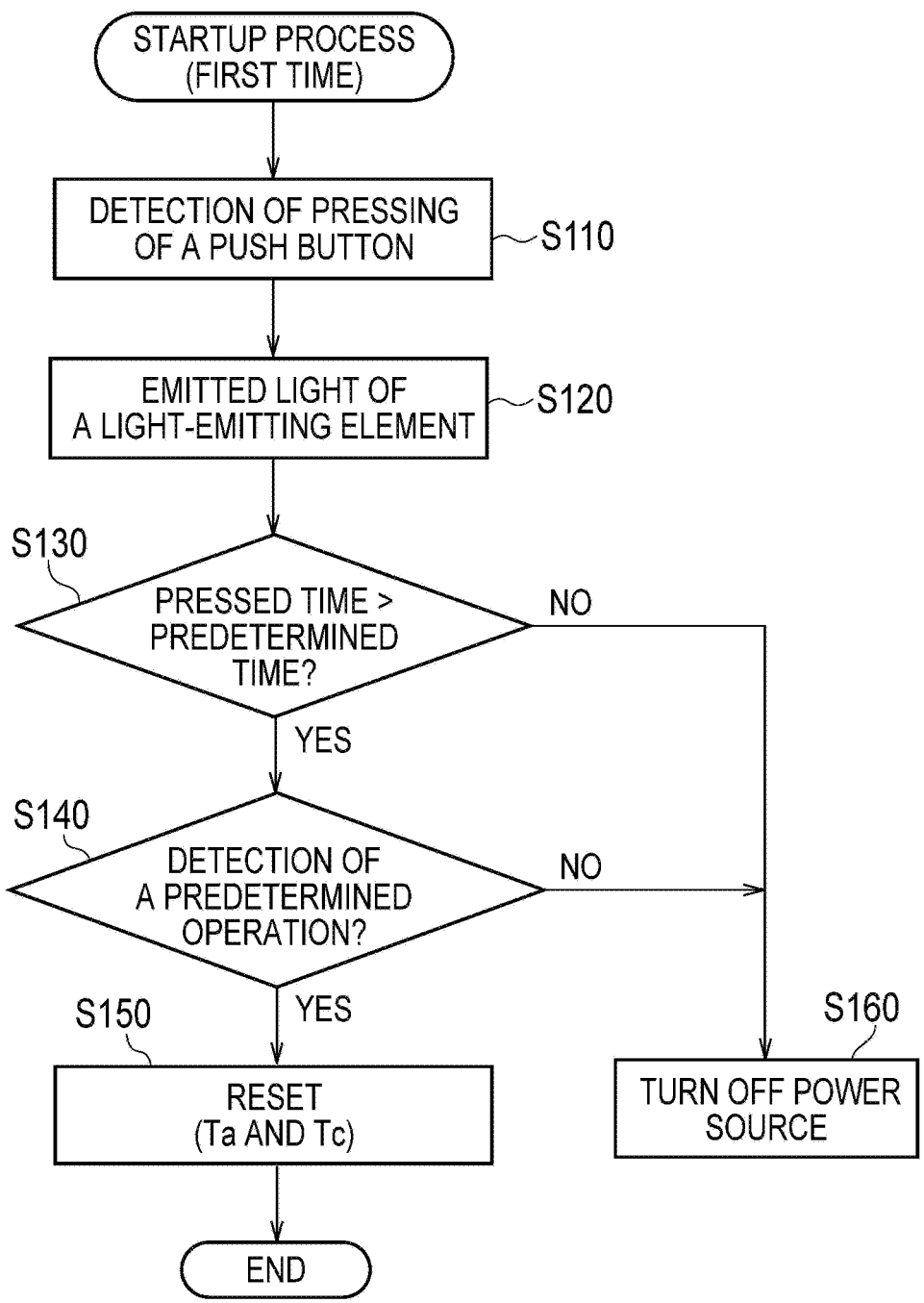
FIG. 11 is a flowchart showing a startup/end process according to the first embodiment.

The startup process (first time) will be described in detail, below. FIG. 11 is a flowchart showing the details of the startup process (first time).

Specifically, as shown in FIG. 11, in step S110, the control circuit 50 detects pressing of the push button 30.

In step S120, the control circuit 50 notifies the user that the power source 10 has been turned ON through the emitted light (for example, lighting of the LED in red color) of the light-emitting element 40. It is noted that such an emitted light of the light-emitting element 40 may be considered as notification that the current puff action series is the puff action series of the first time.

In step S130, the control circuit 50 determines whether or not the pressed time of the push button 30 exceeds a predetermined time. When the determination result is YES, the control circuit 50 moves to a process of step S140. When the determination result is NO, the control circuit 50 moves to a process of step S160.

In step S140, the control circuit 50 determines whether or not a predetermined operation has been performed. The predetermined operation is, for example, an operation of pressing the push button 30 twice within two seconds of lighting out of the LED (lit up in red color) lit up in step S120. The operation detected in step S140 is an example of the above-described second operation.

In step S150, the control circuit 50 resets the second cumulative time period (Ta) and the first cumulative time period (Tc).

In step S160, the control circuit 50 cuts off the power source 10.

(Startup Process (Second Time and Thereafter))

Figure 12:
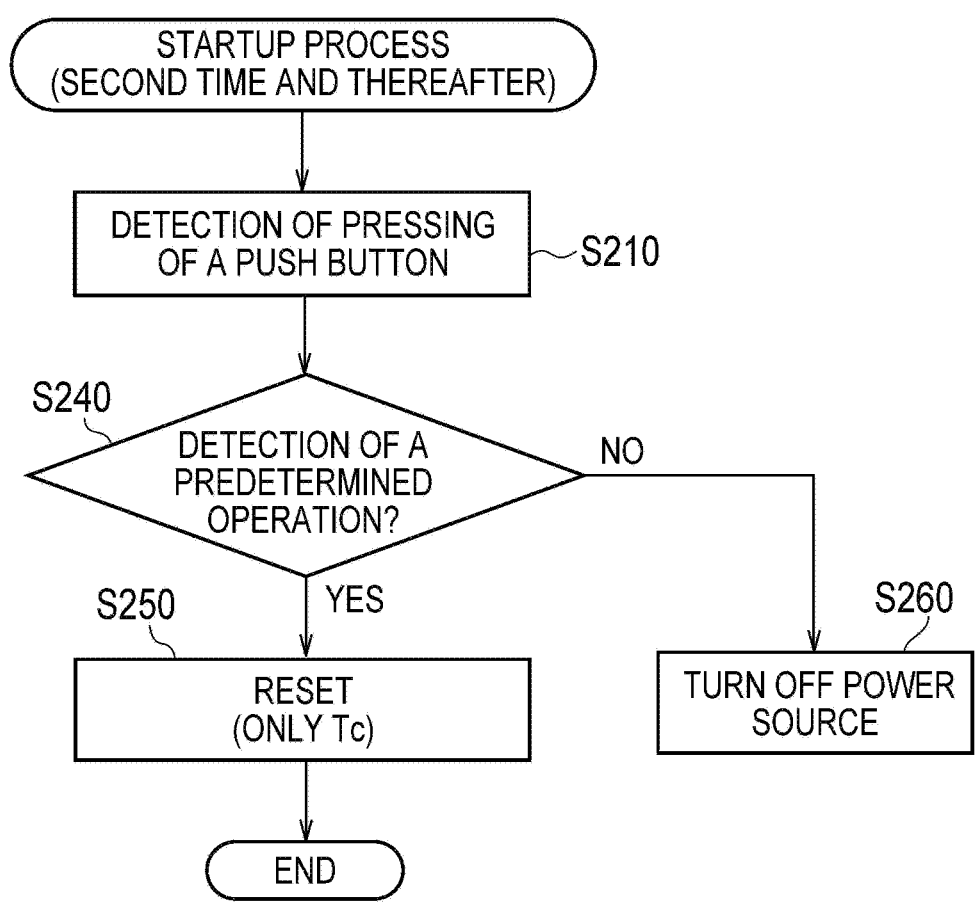
FIG. 12 is a flowchart showing a startup/end process according to the first embodiment.

The startup process (second time and thereafter) will be described in detail, below. FIG. 12 is a flowchart showing the details of the startup process (first time).

Specifically, as shown in FIG. 12, in step S210, the control circuit 50 detects pressing of the push button 30.

In step S240, the control circuit 50 determines whether or not a predetermined operation has been performed. The predetermined operation is, for example, an operation of pressing the push button 30 twice within two seconds. The operation detected in step S240 is an example of the above-described first operation.

In step S250, the control circuit 50 resets the first cumulative time period (Tc).

In step S260, the control circuit 50 cuts off the power source 10.

(Action Monitoring Process)

Figure 13:
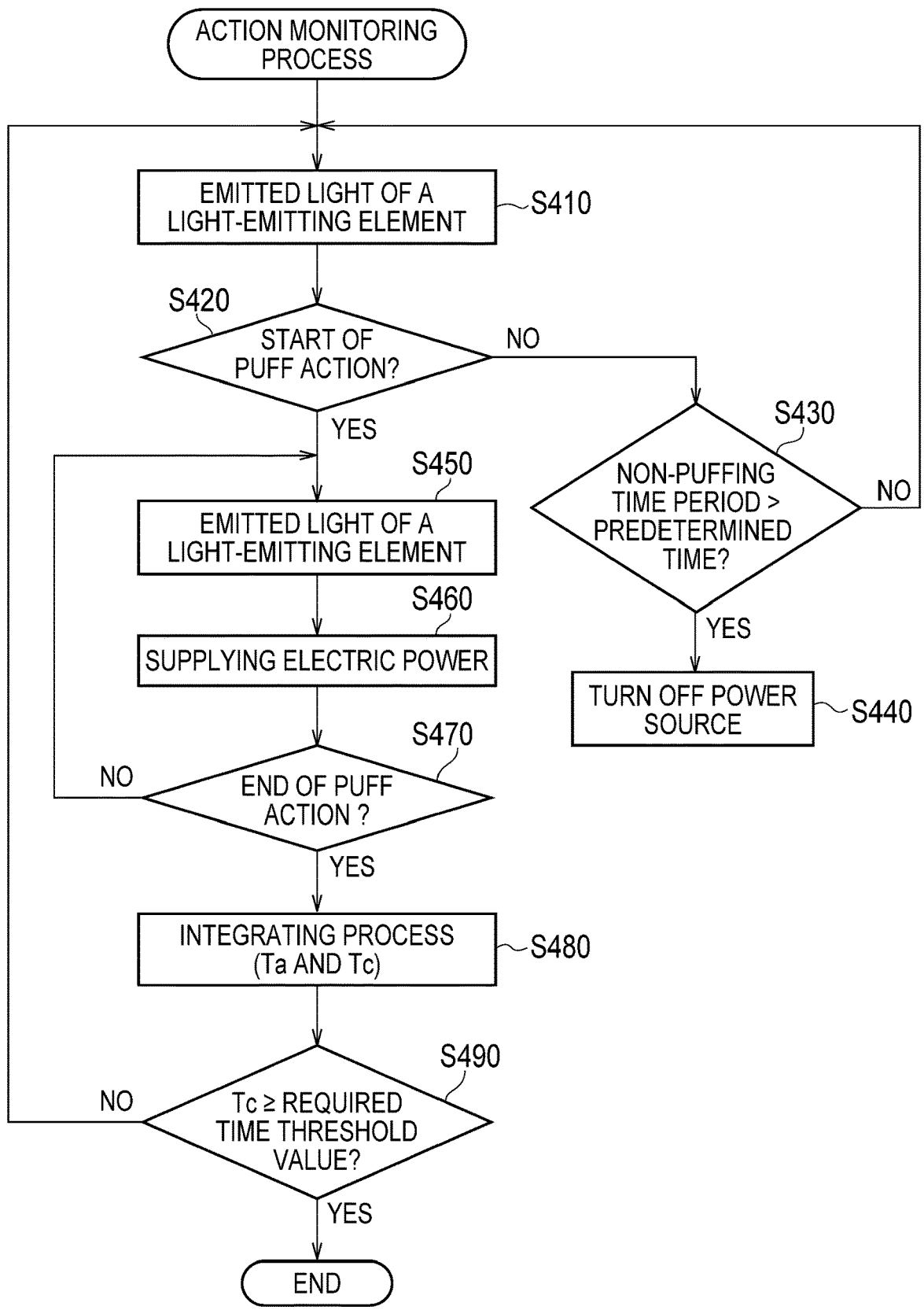
FIG. 13 is a flowchart showing a startup/end process according to the first embodiment.

The action monitoring process will be described in detail, below. FIG. 13 is a flowchart showing the details of the action monitoring process.

Specifically, as shown in FIG. 13, in step S410, the control circuit 50 notifies the user that the current state is a non-puffing state through the emitted light (for example, blinking of the LED in green color at an interval of five seconds) of the light-emitting element 40.

In step S420, the control circuit 50 detects whether or not a puff action has started. When the determination result is YES, the control circuit 50 moves to a process of step S450. When the determination result is NO, the control circuit 50 moves to a process of step S430.

In step S430, the control circuit 50 determines whether or not the time period of the current non-puffing state (non-puffing time period) is equal to or more than a predetermined time period (for example, one minute). When the determination result is YES, the control circuit 50 moves to a process of step S440. When the determination result is NO, the control circuit 50 returns to the process of step S410.

In step S440, the control circuit 50 cuts off the power source 10 by determining that the smoking action is not performed and the puff action series has ended.

In step S450, the control circuit 50 notifies the user that the current state is a puffing state through the emitted light (for example, lighting of the LED in white color) of the light-emitting element 40.

In step S460, the control circuit 50 supplies electric power to the heat source 80. The method of supplying electric power to the heat source 80 in the puffing state is as described above.

In step S470, the control circuit 50 detects whether or not a puff action has ended. When the determination result is YES, the control circuit 50 moves to a process of step S480. When the determination result is NO, the control circuit 50 returns to the process of step S450.

In step S480, the control circuit 50 integrates the second cumulative time period (Ta) and the first cumulative time period (Tc). Specifically, the time interval of performing the step S480 is possible to be counted by a clock of the control circuit 50, and the control circuit 50 adds the time interval of performing step S480 to the second cumulative time period (Ta) and the first cumulative time period (Tc).

In step S490, the control circuit 50 determines whether or not the first cumulative time period (Tc) is equal to or above the required time threshold value. When the determination result is YES, the control circuit 50 ends the action monitoring process, and moves to the end determination process. When the determination result is NO, the control circuit 50 returns to the process of step S410.

(End Determination Process)

Figure 14:
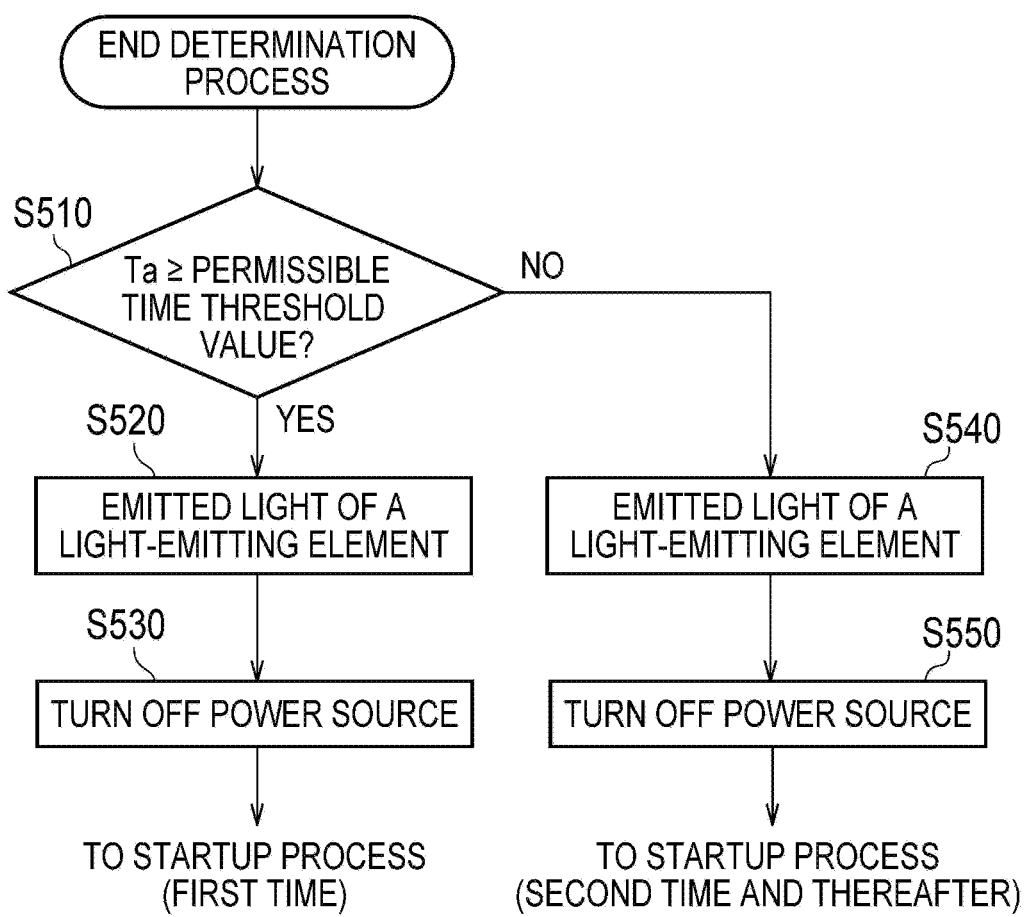
FIG. 14 is a flowchart showing a startup/end process according to the first embodiment.

The end determination process will be described in detail, below. FIG. 14 is a flowchart showing the details of the end determination process.

Specifically, as shown in FIG. 14, in step S510, the control circuit 50 determines whether or not the second cumulative time period (Ta) is equal to or above the permissible time threshold value. When the determination result is YES, the control circuit 50 moves to a process of step S520. When the determination result is NO, the control circuit 50 moves to a process of step S540.

In step S520, the control circuit 50 notifies the user that it is necessary to replace the second unit through the emitted light (for example, reducing the luminosity of the LED after lighting up the LED in red color, and finally, lighting out the LED) of the light-emitting element 40.

In step S530, the control circuit 50 cuts off the power source 10 in order to end the puff action series. It must be noted that if the power source 10 is turned ON again after the power source 10 is cut off in the process of step S530, the process of step S100 (startup process (first time)) is performed from among the step S100 and the step S200 shown in FIG. 10.

In step S540, the control circuit 50 notifies the user that it is not necessary to replace the second unit through the emitted light (for example, reducing the luminosity of the LED after lighting up the LED in white color, and finally, lighting out the LED) of the light-emitting element 40. It must be noted that the light-emitting mode of the light-emitting element 40 in step S540 is different from the light-emitting mode of the light-emitting element 40 in step S520.

In step S550, the control circuit 50 cuts off the power source 10 in order to end the puff action series. It must be noted that if the power source 10 is turned ON again after the power source 10 is cut off in the process of step S550, the process of step S200 (startup process (second time and thereafter)) is performed from among the step S100 and the step S200 shown in FIG. 10.

In the first embodiment, the determination process of step S490 (comparison process of the first cumulative time period (Tc) and the required time threshold value) is performed prior to the determination process of step S510 (comparison process of the second cumulative time period (Ta) and the permissible time threshold value). That is, when the second cumulative time period (Ta) has reached the permissible time threshold value, but the first cumulative time period (Tc) has not reached the required time threshold value, the control circuit 50 does not cut off the power source 10, and continues the supply of electric power to the heat source 80.

As described above, after the end of the one-time puff action series is notified by the light-emitting mode of the light-emitting element 40, the power source 10 of the non-burning type flavor inhaler 100 is cut off. However, the embodiment is not limited thereto. That is, the end of the one-time puff action series may be notified by stopping the supply of electric power to the heat source 80 before the end of the one-time puff action series is notified by the light-emitting mode of the light-emitting element 40. In such a case, the end of the one-time puff action series is notified by both stopping of the supply of electric power to the heat source 80 and the light-emitting mode of the light-emitting element 40.

(Operation and Effect)

In the first embodiment, considering the fact that the permissible time specified in the second unit (the capsule unit 130) is longer than the required time as a prerequisite, the control circuit 50 notifies the end of the one-time puff action series when the first cumulative amount of electric power reaches the required amount of electric power. As a result, even if the permissible time specified in the second unit (for example, the capsule unit 130) is longer than the required time, the user is capable of understanding the timing when the puff action series needs to be ended, with the similar sense of use as a regular cigarette.

In the first embodiment, when the second cumulative amount of electric power has reached the permissible amount of electric power, but the first cumulative amount of electric power has not reached the required amount of electric power, the control circuit 50 does not cut off the power source 10, and continues the supply of electric power to the heat source 80. As a result, since the second cumulative amount of electric power exceeds the permissible amount of electric power, it is not possible to supply a sufficient amount of aerosol in the next puff action series, but nevertheless, in the current puff action series, even though the second cumulative amount of electric power exceeds the permissible amount of electric power, it is possible to enjoy an amount of aerosol (or inhaling flavor) equal to the amount to be supplied in the puff action series, and then it is possible to prevent the forcible end of smoking in the course of the puff action series.

In the first embodiment, when the second cumulative amount of electric power reaches the permissible amount of electric power, the control circuit 50 notifies that the second unit must be replaced, by the light-emitting mode of the light-emitting element 40. As a result, the user is capable of understanding the timing of replacement of the second unit (here, the capsule unit 130).

In the first embodiment, the control circuit 50 resets the first cumulative amount of electric power by the first operation, and resets the second cumulative amount of electric power by the second operation that is different from the first operation. That is, since an explicit second operation by the user is required for resetting the second cumulative amount of electric power, it is possible to appropriately urge the user to replace the second unit.

In the first embodiment, in the non-puffing state in which aerosol is not inhaled, the light-emitting element controller 52 controls the light-emitting element 40 according to the second light-emitting mode that is different from the first light-emitting mode. As a result, even in the non-puffing state, it is possible to make the user understand whether or not the non-burning type flavor inhaler 100 is in a usable state. Further, since the light-emitting mode in the puffing state is different from the light-emitting mode in the non-puffing state, it is possible to realize a sense of use that resembles the sense of use of a regular cigarette in which aerosol is generated in association with burning.

In the first embodiment, the second light-emitting mode changes in accordance with the number of times of the puff action of inhaling aerosol. As a result, in the non-puffing state in which the emitted light of the light-emitting element 40 is easily visually recognized, the user is capable of easily understanding the progress status of puffing by the change in the second light-emitting mode.

In the first embodiment, the heat source controller 53 gradually increases the amount of electric power supplied to the heat source 80 from the standard amount of electric power with an increase in the number of times of the puff action of inhaling the aerosol. As a result, it is possible to bring the amount of supply of the aerosol closer to that of the regular cigarette in which aerosol is generated in association with burning, and it is possible to realize a sense of use that resembles that of a regular cigarette.

In the first embodiment, the heat source controller 53 controls the first mode in which the first standard amount of electric power is used as the standard amount of electric power, and the second mode in which the second standard amount of electric power that is greater than the first standard amount of electric power is used as the standard amount of electric power. As a result, it is possible for the user to select an aerosol amount in accordance with a preference of the user, with a single non-burning type flavor inhaler 100.

In the first embodiment, even in the case of a user for whom the required time of a one-time puff action is shorter than the standard required time, it is possible to improve the level of satisfaction of such a user by raising the temperature of the heat source faster than the standard mode by introducing the shortened mode. Regardless of the action mode, since the amount of electric power supplied to the heat source is reduced for the duration after the first time period or the third time period has elapsed, inhaling of decomposed substances is prevented, and a drop in flavor is also prevented.

In the first embodiment, the predetermined action mode (standard mode and shortened mode) is provided, and thus it may be favorable to control the amount of electric power supplied to the heat source according to the predetermined action mode. As a result, during the period when electric power is being supplied to the heat source 80, complex control such as continuous control of the amount of supply of the electric power on the basis of the air flow (inhalation rate) is not necessary. In other words, it is possible to realize a drop in the flavor, and an improvement in the level of satisfaction of the user, with a simple configuration.

[First Modification]

A first modification of the first embodiment will be described, below. Description proceeds with a particular focus on a difference from the first embodiment, below.

Specifically, in the above-described first embodiment, the heat source controller 53 controls the amount of electric power supplied to the heat source 80 from the power source 10 by controlling the voltage applied to the heat source 80 from the power source 10. In particular, the heat source controller 53 gradually increases the amount of electric power (voltage) supplied to the heat source 80 from the standard amount of electric power (standard voltage) with an increase in the number of times of the puff action of inhaling the aerosol (see FIG. 7).

In contrast, in the first modification, the heat source controller 53 controls the voltage that is applied to the heat source 80 from the power source 10 by pulse control, and controls the amount of electric power supplied to the heat source 80 from the power source 10 by controlling the pulse width (Duty ratio) at which the voltage is applied to the heat source 80. In particular, the heat source controller 53 gradually shortens the pulse width at which the voltage is applied to the heat source 80 from the standard pulse width with an increase in the number of times of the puff action of inhaling the aerosol (see FIG. 15).

Figure 15:
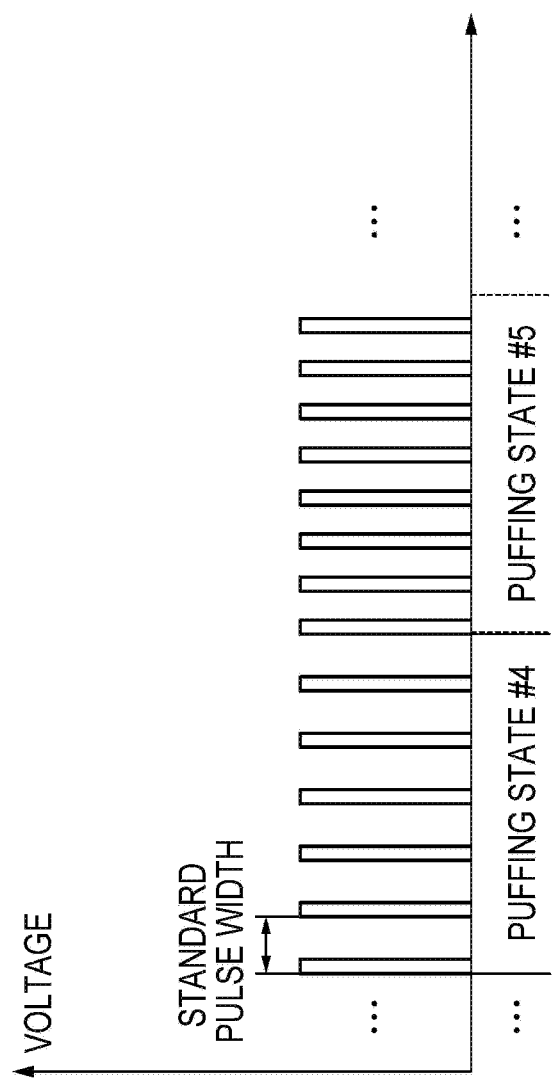
FIG. 15 is a diagram showing an example of power control in a puff action series according to a first modification.

It is noted that following the example shown in FIG. 7, FIG. 15 illustrates a case in which the amount of electric power is increased between the puffing state #4 and the puffing state #5. Although the puffing states other than the puffing state #4 and the puffing state #5 are omitted in FIG. 15, it is a matter of course that a similar effect as in the example shown in FIG. 7 is obtained by controlling the pulse width (Duty ratio).

[Second Modification]

A second modification of the first embodiment will be described, below. Description proceeds with a particular focus on a difference from the first embodiment, below.

Specifically, in the above-described first embodiment, the heat source controller 53 controls the amount of electric power supplied to the heat source 80 from the power source 10 by controlling the voltage applied to the heat source 80 from the power source 10. In particular, the heat source controller 53 gradually increases the amount of electric power (voltage) supplied to the heat source 80 from the standard amount of electric power (standard voltage) with an increase in the number of times of the puff action of inhaling the aerosol (see FIG. 7).

Figure 16:
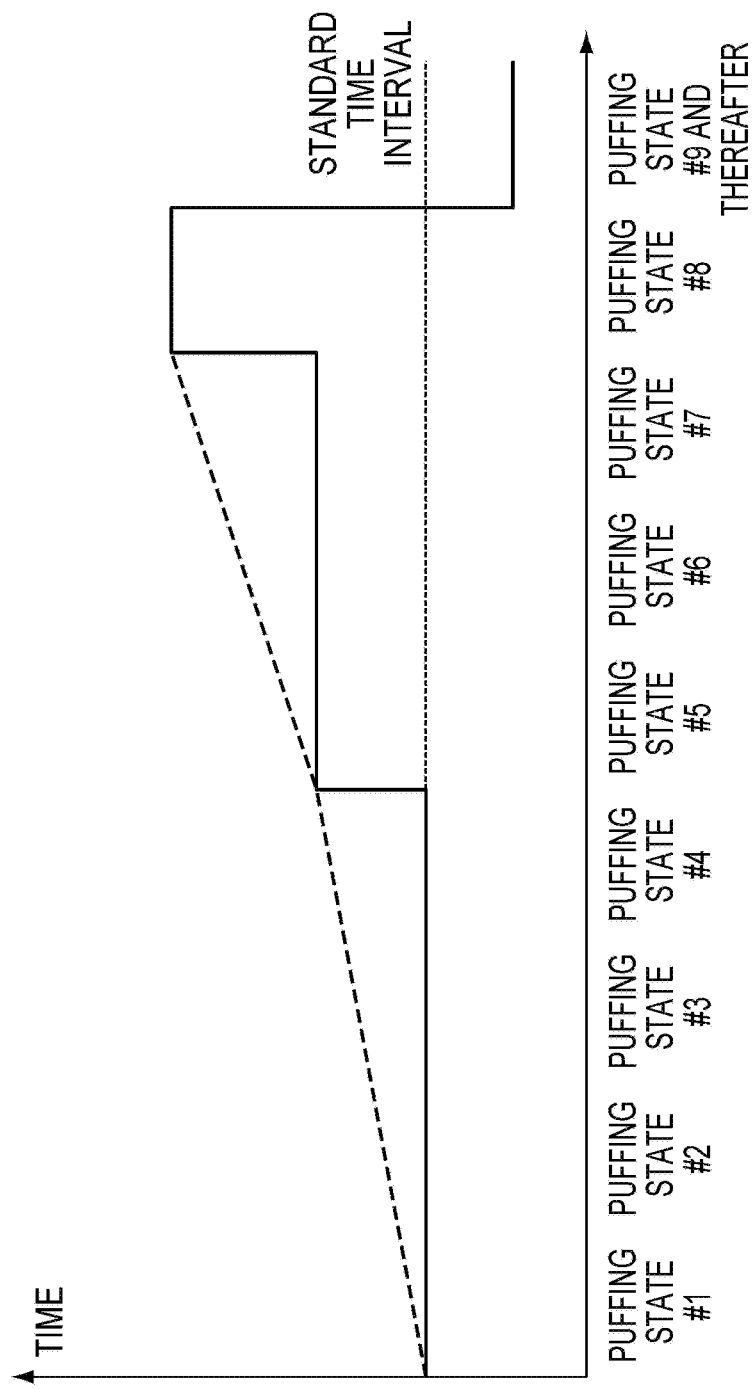
FIG. 16 is a diagram showing an example of power control in a puff action series according to a second modification.

In contrast, in the second modification, the heat source controller 53 controls the amount of electric power supplied to the heat source 80 from the power source 10 by controlling the time interval during which the voltage is applied to the heat source 80. In particular, the heat source controller 53 gradually extends the time interval during which the voltage is applied to the heat source 80 from the standard time interval with an increase in the number of times of the puff action of inhaling the aerosol (see FIG. 16).

In the second modification, the standard time interval implies the maximum time for which the application of voltage to the heat source 80 is continued when the user continues the puff action. Therefore, if the time period during which the user continues the puff action exceeds the standard time interval, the application of voltage to the heat source 80 stops. It is noted that even if the application of voltage stops, the first light-emitting mode of the light-emitting element 40 is maintained during the time the puff action of the user continues. As a result, since the total amount of electric power supplied to the heat source 80 in a one-time puff action changes, the similar effect as in the example shown in FIG. 7 is obtained.

It is noted that when the standard mode and the shortened mode described in the first embodiment are introduced, the first time period, the second time period, and the third time period may be adjusted (extended) with an increase in the number of times of the puff action of inhaling the aerosol.

Other Embodiments

The present invention is described through the above-described embodiments, but it should not be understood that this invention is limited by the statements and the drawings constituting a part of this disclosure. From this disclosure, various alternative embodiments, examples, and operational technologies will become apparent to those skilled in the art.

In the embodiment, although not particularly mentioned, the number of times of the puff action may be corrected by a value (the amount of generation of the aerosol) defined by the required time of a one-time puff action and the amount of electric power supplied to the heat source 80. Specifically, if the amount of the aerosol generated in a one-time puff action is less than the default value, the number of times of the puff action may be accumulated by adding a value obtained by multiplying a predetermined coefficient α (α<1) once. On the other hand, if the amount of the aerosol generated in a one-time puff action is more than the default value, the number of times of the puff action may be accumulated by adding a value obtained by multiplying a predetermined coefficient β (β>1) once. That is, the number of times of the puff action need not necessarily be an integer.

In the embodiment, a puff action series is a series of actions in which the puff action is repeated a predetermined number of times (for example, eight times). Here, the predetermined number of times may be the number of times of the puff action that is performed with a regular cigarette in which aerosol is generated in association with burning. Alternatively, the predetermined number of times may be defined in accordance with the desired amount of generation of the aerosol that the user must inhale in a puff action series.

In the embodiment, the permissible amount of electric power, the required amount of electric power, the first cumulative amount of electric power, and the second cumulative amount of electric power have been described as values that are managed only by time, by assuming that the electric power (voltage or current) is fixed. However, the embodiment is not limited thereto. If it is not assumed that the electric power (voltage or current) is fixed, the permissible time threshold value, the required amount of electric power, the first cumulative time period (Tc), and the second cumulative time period (Ta) may be corrected by a value (the amount of generation of the aerosol) that is defined by the amount of electric power supplied to the heat source 80.

In the embodiment, the control unit is provided in the first unit; however, the embodiment is not limited thereto. The control unit may be provided in the second unit. Alternatively, the control unit may be provided in the first unit and the second unit, respectively. Else, a part of the control unit may be provided in the first unit, and the other part of the control unit may be provided in the second unit, and thus the control unit may be configured to realize the functions of the control unit in a state in which the second unit is attached to the first unit.

In the embodiment, although not particularly mentioned, in the power control of the puff action series, the timing of increasing the amount of electric power supplied to the heat source 80 is preferably synchronized with the timing of changing the second light-emitting mode. For example, as shown in FIG. 6 and FIG. 7, when the amount of electric power (voltage) supplied to the heat source 80 increases between the puffing state #4 and the puffing state #5, the second light-emitting mode preferably changes between the puffing state #4 and the puffing state #5.

In the embodiment, although not particularly specified, as shown in FIG. 8 and FIG. 9, a voltage that is smaller than the standard voltage is applied to the heat source 80 for the duration after the first time period T1 or the third time period T3 has elapsed; however, the first light-emitting mode preferably continues even for such a duration.

In the embodiment, the first mode (Low mode shown in FIG. 6) in which the first standard amount of electric power is used as the standard amount of electric power, and the second mode (High mode shown in FIG. 7) in which the second standard amount of electric power that is greater than the first standard amount of electric power is used as the standard amount of electric power, are provided. In such a case, the light-emitting mode of the first mode may be different from the light-emitting mode of the second mode. That is, each of the first light-emitting mode, the second light-emitting mode, and the end light-emitting mode of the first mode may be different from the first light-emitting mode, the second light-emitting mode, and the end light-emitting mode of the second mode.

In the embodiment, the electrical unit 110 and the atomization unit 120 configure the first unit having the non-mouthpiece end. On the other hand, the capsule unit 130 configures the second unit that is configured in a removable manner with respect to the first unit. However, the embodiment is not limited thereto.

For example, the electrical unit 110 may configure the first unit having the non-mouthpiece end, and the atomization unit 120 having the aerosol source may configure the second unit that is attached in a removable manner with respect to the first unit. In such a case, the permissible amount of electric power is defined in accordance with the life of the aerosol source. In such a case, the non-burning type flavor inhaler 100 may not have a solid flavor source 131, but may have a liquid flavor source (for example, a tobacco-derived inhaling flavor component (such as nicotine), and an essence component such as menthol, etc.). It is possible to use glycerine or propylene glycol, etc. as the aerosol source. Further, the above-described holder 60 preferably holds the liquid flavor source and the aerosol source.

Alternatively, the electrical unit 110 may configure the first unit having the non-mouthpiece end, and the atomization unit 120 having the aerosol source and the capsule unit 130 having the flavor source 131 may configure the second unit that is attached in a removable manner with respect to the first unit. In such a case, the permissible amount of electric power is defined in accordance with the shorter life of the life of the flavor source 131 and the life of the aerosol source.

In the embodiment, a case is illustrated in which the second unit is attached to the first unit in a removable manner. However, the embodiment is not limited thereto. Specifically, instead of considering the removal of the second unit from the first unit as a prerequisite, the first unit and the second unit may be integrally configured after attaching the second unit to the first unit. That is, the embodiment may be applied to non-burning type flavor inhaler 100 of a disposable type. In such a case, it is not necessary to reset the second cumulative time period (Ta).

In the embodiment, when the second cumulative time period (Ta) reaches the permissible time threshold value, and the first cumulative time period (Tc) reaches the required time threshold value, the control circuit 50 notifies that the second unit must be replaced, by the light-emitting mode of the light-emitting element 40. In other words, when the second cumulative amount of electric power reaches the permissible amount of electric power, and the first cumulative amount of electric power reaches the required amount of electric power, the control circuit 50 notifies that the second unit must be replaced, by the light-emitting mode of the light-emitting element 40. However, the embodiment is not limited thereto. Specifically, when the second cumulative time period (Ta) reaches the permissible time threshold value even before the first cumulative time period (Tc) reaches the required time threshold value, the control circuit 50 may notify that the second unit must be replaced, by the light-emitting mode of the light-emitting element 40. In other words, when the second cumulative amount of electric power reaches the permissible amount of electric power even before the first cumulative amount of electric power reaches the required amount of electric power, the control circuit 50 may notify that the second unit must be replaced, by the light-emitting mode of the light-emitting element 40.

Although not particularly mentioned in the embodiments, a program may be provided, which is configured to cause a computer to execute each process performed by the non-burning type flavor inhaler 100. Further, the program may be recorded on a computer-readable medium. By using the computer-readable medium, it is possible to install the program in a computer. Here, the computer-readable medium in which the program is recorded thereon may include a non-transitory recording medium. The non-transitory recording medium is not particularly limited; the non-transitory recording medium may include a recording medium such as a CD-ROM or a DVD-ROM, for example.

Alternatively, a chip may be provided which is configured by: a memory in which a program for executing each process performed by the non-burning type flavor inhaler 100 is stored; and a processor configured to execute the program stored in the memory.

It is noted that the entire content of Japanese Patent Application No. 2014-095160 (filed on May 2, 2014) is incorporated in the subject application by reference.

INDUSTRIAL APPLICABILITY

According to the embodiment, it is possible to provide a non-burning type flavor inhaler and a computer-readable medium by which it is possible to understand the timing when the puff action series needs to be ended with the similar sense of use as a regular cigarette even if the permissible time specified in the second unit (for example, the flavor source or the aerosol source) is longer than the required time.

The invention claimed is:

1. A non-burning type flavor inhaler having a shape extending along a predetermined direction from a non-mouthpiece end toward a mouthpiece end, comprising:
   a first unit having the non-mouthpiece end;
   a second unit attachable to the first unit;
   a control circuit configured to control the non-burning type flavor inhaler; and
   a sensor connected to the control circuit for detecting a wind pressure generated by an inhale action of the user in order for the control circuit to detect a puffing state, wherein
   the second unit includes at least one of an aerosol source generating aerosol and a flavor source,
   the non-burning type flavor inhaler includes an electric heat source configured to heat the aerosol source or the flavor source without burning, and a power source configured to supply electric power to the electric heat source,
   the control circuit is configured to permit the electric power to be supplied up to a permissible amount of electric power that is larger than a required amount of electric power, wherein the permissible amount of electric power is defined by a cumulative value of an amount of electric power that is permitted to be supplied to the electric heat source after attaching the second unit to the first unit, and the required amount of electric power is a preset value of an amount of electric power to be supplied to the electric heat source in a one-time puff action series which is a series of actions in which a puff action is repeated a predetermined number of times, and
   the control circuit includes a clock which is configured to count a first time interval such that the control circuit is configured to integrate, using the first time interval, a first cumulative amount of electric power which is a cumulative value of the amount of electric power supplied to the electric heat source in the one-time puff action series during a use of the non-burning type flavor inhaler, and to notify an end of the one-time puff action series when the first cumulative amount of electric power is determined by the control circuit during the use of the non-burning type flavor inhaler to reach the required amount of electric power.

2. The non-burning type flavor inhaler according to claim 1, wherein
   the permissible amount of electric power is greater than two times of the required amount of electric power.

3. The non-burning type flavor inhaler according to claim 1, wherein
   the control circuit is configured to notify the end of the one-time puff action series by stopping a supply of electric power to the electric heat source.

4. The non-burning type flavor inhaler according to claim 1, wherein
   the control circuit is configured to notify the end of the one-time puff action series by a light-emitting mode of a light-emitting element.

5. The non-burning type flavor inhaler according to claim 3, wherein
   the control circuit is configured to integrate a second cumulative amount of electric power which is a cumulative value of the amount of electric power supplied to the electric heat source after attaching the second unit to the first unit during the use of the non-burning type flavor inhaler, and when the second cumulative amount of electric power reaches the permissible amount of electric power, but the first cumulative amount of electric power does not reach the required amount of electric power, the control circuit does not cut off the electric power source, and continues the supply of electric power to the electric heat source until the first cumulative amount of electric power reaches the required amount of electric power.

6. The non-burning type flavor inhaler according to claim 5, wherein
when the second cumulative amount of electric power reaches the permissible amount of electric power, the control circuit is configured to notify that the second unit must be replaced, by a light-emitting mode of a light-emitting element.

7. The non-burning type flavor inhaler according to claim 5, wherein
when the second cumulative amount of electric power reaches the permissible amount of electric power, and when the first cumulative amount of electric power reaches the required amount of electric power, the control circuit is configured to notify that the second unit must be replaced, by a light-emitting mode of a light-emitting element.

8. The non-burning type flavor inhaler according to claim 5, wherein
the control circuit is configured to reset the first cumulative amount of electric power by a first operation, and resets the second cumulative amount of electric power by a second operation that is different from the first operation.

9. The non-burning type flavor inhaler according to claim 1, wherein
the permissible amount of electric power is determined in accordance with a life of the flavor source in a case where the second unit has the flavor source.

10. The non-burning type flavor inhaler according to claim 1, wherein
the permissible amount of electric power is determined in accordance with a life of the aerosol source in a case where the second unit has the aerosol source.

11. The non-burning type flavor inhaler according to claim 1, wherein
the permissible amount of electric power is determined in accordance with a shorter life of a life of the flavor source and a life of the aerosol source in a case where the second unit has the flavor source and the aerosol source.

12. A computer-readable medium recorded a program used in a non-burning type flavor inhaler having a shape extending along a predetermined direction from a non-mouthpiece end toward a mouthpiece end, wherein
the non-burning type flavor inhaler includes a first unit having the non-mouthpiece end, a second unit attached to the first unit, and a sensor configured for detecting a wind pressure generated by an inhale action of the user in order to detect a puffing state,
the second unit includes an aerosol source generating aerosol or a flavor source,
the non-burning type flavor inhaler includes an electric heat source configured to heat the aerosol source or the flavor source without burning, and a power source configured to supply electric power to the electric heat source,
the program causes a computer to execute a control of the non-burning type flavor inhaler including:
permitting the electric power to be supplied up to a permissible amount of electric power that is larger than a required amount of electric power, wherein the permissible amount of electric power is defined by a cumulative value of an amount of electric power that is permitted to be supplied to the electric heat source after attaching the second unit to the first unit, and the required amount of electric power is a preset value of an amount of electric power to be supplied to the electric heat source in a one-time puff action series which is a series of actions in which a puff action is repeated a predetermined number of times, and
integrating using a first time interval, counted by a clock, a first cumulative amount of electric power which is a cumulative value of the amount of electric power supplied to the electric heat source in the one-time puff action series during a use of the non-burning type flavor inhaler, and to notify an end of the one-time puff action series when the first cumulative amount of electric power is determined by the computer during the use of the non-burning type flavor inhaler to reach the required amount of electric power.

* * * * *